United States Patent
Shupe et al.

(10) Patent No.: US 12,232,815 B2
(45) Date of Patent: Feb. 25, 2025

(54) SURGICAL PLANNING AND METHOD

(71) Applicant: DePuy Ireland Unlimited Company, County Cork (IE)

(72) Inventors: Sarah J. Shupe, Winona Lake, IN (US); Michael Joseph Rock, Pudsey (GB); David Robert Wolfson, Leeds (GB); Gianpaolo Fusari, London (GB); Hawys Eleri Tomos, London (GB); Robert Edward Matthews, London (GB); John Naybour, Artarmon (AU); Mark Heldreth, Mentone, IN (US)

(73) Assignee: DEPUY IRELAND UNLIMITED COMPANY, LOUGHBEG INDUSTRIAL ESTATE, Cork (IE)

( * ) Notice: Subject to any disclaimer, the term of this patent is extended or adjusted under 35 U.S.C. 154(b) by 0 days.

(21) Appl. No.: 18/205,803

(22) Filed: Jun. 5, 2023

(65) Prior Publication Data
US 2023/0310081 A1 Oct. 5, 2023

Related U.S. Application Data

(60) Continuation of application No. 17/155,194, filed on Jan. 22, 2021, now Pat. No. 11,701,177, which is a
(Continued)

(51) Int. Cl.
*A61B 34/10* (2016.01)
*A61B 17/15* (2006.01)
(Continued)

(52) U.S. Cl.
CPC ............ *A61B 34/10* (2016.02); *A61B 17/155* (2013.01); *A61B 17/157* (2013.01);
(Continued)

(58) Field of Classification Search
CPC .............. A61B 34/10; A61B 2034/101; A61B 2034/104; A61B 2034/105
See application file for complete search history.

(56) References Cited

U.S. PATENT DOCUMENTS

| 4,207,627 A | 6/1980 | Cloutier |
| 4,822,366 A | 4/1989 | Bolesky |

(Continued)

FOREIGN PATENT DOCUMENTS

| AU | 2012262079 B2 | 12/2013 |
| EP | 2416740 B1 | 2/2012 |

(Continued)

OTHER PUBLICATIONS

Australian Search Report for Corresponding Australian App. No. 2015320707 Dated Feb. 7, 2020 (Feb. 6, 2020), 6 Pages.

(Continued)

*Primary Examiner* — Nicholas W Woodall

(57) ABSTRACT

Methods and apparatus for planning and/or carrying out a total knee replacement surgical procedure on a knee of a leg of a patient are described. Anatomical data for the leg of the patient is obtained, which allows the femoral mechanical axis, the tibial mechanical axis, and the joint line of the knee to be determined. A planned proximal tibial cut angle and a planned distal femoral cut angle are determined. A total knee replacement procedure is carried out on the knee of the patient such that a distal femoral cut is made using the planned distal femoral cut angle and a proximal tibial cut is made using the planned proximal tibial cut angle.

3 Claims, 11 Drawing Sheets

Related U.S. Application Data division of application No. 15/504,152, filed as application No. PCT/US2015/051672 on Sep. 23, 2015, now Pat. No. 10,932,855.

(60) Provisional application No. 62/054,604, filed on Sep. 24, 2014.

(51) Int. Cl.
*A61B 17/56* (2006.01)
*A61F 2/38* (2006.01)
*A61B 34/20* (2016.01)
*A61F 2/46* (2006.01)

(52) U.S. Cl.
CPC ... *A61B 2017/564* (2013.01); *A61B 2034/104* (2016.02); *A61B 2034/105* (2016.02); *A61B 2034/108* (2016.02); *A61B 2034/2046* (2016.02); *A61F 2/38* (2013.01); *A61F 2002/4633* (2013.01)

(56) References Cited

U.S. PATENT DOCUMENTS

| | | | |
|---|---|---|---|
| 4,952,213 A | 8/1990 | Bowman | |
| 5,035,699 A * | 7/1991 | Coates | A61B 17/155 606/86 R |
| 5,133,759 A | 7/1992 | Turner | |
| 5,258,032 A * | 11/1993 | Bertin | A61B 17/155 606/88 |
| 5,275,603 A | 1/1994 | Ferrante | |
| 5,326,361 A | 7/1994 | Hollister | |
| 5,370,692 A | 12/1994 | Fink | |
| 5,681,316 A | 10/1997 | Deorio | |
| 5,681,354 A | 10/1997 | Eckhoff | |
| 5,682,886 A | 11/1997 | Delp | |
| 5,688,279 A | 11/1997 | McNulty | |
| 5,824,105 A | 10/1998 | Ries | |
| 5,871,018 A | 2/1999 | Delp | |
| 6,039,764 A | 3/2000 | Pottenger | |
| 6,173,200 B1 | 1/2001 | Cooke | |
| 6,205,411 B1 | 3/2001 | DiGioia, III | |
| 6,459,948 B1 | 10/2002 | Ateshian et al. | |
| 6,858,032 B2 | 2/2005 | Chow | |
| 7,206,626 B2 | 4/2007 | Quaid, III | |
| 7,206,627 B2 | 4/2007 | Abovitz | |
| 7,364,590 B2 | 4/2008 | Siebel | |
| 7,387,644 B2 | 6/2008 | Beynnon | |
| 7,392,076 B2 | 6/2008 | Moctezuma De La Barrerra | |
| 7,468,075 B2 | 12/2008 | Slamin | |
| 7,611,519 B2 | 11/2009 | Lefevre | |
| 7,625,407 B2 | 12/2009 | Akizuki | |
| 7,744,601 B2 | 6/2010 | Rosa | |
| 7,747,311 B2 | 6/2010 | Quaid, III | |
| 7,831,292 B2 | 11/2010 | Quaid | |
| 8,010,180 B2 | 8/2011 | Quaid | |
| 8,078,440 B2 | 12/2011 | Otto | |
| 8,095,200 B2 | 1/2012 | Quaid, III | |
| 8,221,430 B2 | 7/2012 | Park | |
| 8,257,360 B2 | 9/2012 | Richard | |
| 8,298,288 B2 | 10/2012 | Walker | |
| 8,337,564 B2 | 12/2012 | Shah | |
| 8,419,741 B2 | 4/2013 | Carignan et al. | |
| 8,425,617 B2 | 4/2013 | Otto | |
| 8,475,535 B2 | 4/2013 | Carignan | |
| 8,617,171 B2 | 7/2013 | Otto | |
| 8,535,383 B2 | 9/2013 | Aram | |
| 8,641,721 B2 | 2/2014 | Aram et al. | |
| 8,652,210 B2 | 2/2014 | Otto | |
| 8,794,977 B2 | 8/2014 | Mcguan | |
| 8,983,813 B2 | 3/2015 | Miles | |
| 8,996,169 B2 | 3/2015 | Lightcap | |
| 9,532,845 B1 | 1/2017 | Dossett | |
| 9,801,686 B2 | 10/2017 | Lightcap | |
| 2005/0070910 A1 | 3/2005 | Keene | |
| 2006/0136058 A1 | 6/2006 | Pietrzak | |
| 2006/0142657 A1 | 6/2006 | Quaid | |
| 2006/0155294 A1 | 7/2006 | Steffensmeier | |
| 2007/0161888 A1 | 7/2007 | Sherman | |
| 2007/0233139 A1 | 10/2007 | Metcalfe | |
| 2008/0058945 A1 | 3/2008 | Hajaj | |
| 2009/0089034 A1 | 4/2009 | Penney | |
| 2009/0209884 A1* | 8/2009 | Van Vorhis | G16H 50/50 600/595 |
| 2009/0240169 A1 | 9/2009 | Warkentine | |
| 2010/0049195 A1 | 2/2010 | Park | |
| 2011/0029093 A1* | 2/2011 | Bojarski | A61B 17/157 623/20.14 |
| 2011/0066080 A1 | 3/2011 | Stifter | |
| 2011/0071531 A1 | 3/2011 | Carson | |
| 2011/0082558 A1 | 4/2011 | Kim | |
| 2011/0092804 A1 | 4/2011 | Achoenefeld | |
| 2011/0106093 A1 | 5/2011 | Romano | |
| 2011/0275957 A1 | 11/2011 | Bhandari | |
| 2012/0095564 A1 | 4/2012 | Mihalko | |
| 2012/0123418 A1 | 5/2012 | Giurgi | |
| 2012/0185054 A1 | 7/2012 | Maloney | |
| 2012/0191205 A1 | 7/2012 | Bojarski et al. | |
| 2012/0310362 A1 | 12/2012 | Li | |
| 2013/0012944 A1 | 1/2013 | Mccombs | |
| 2013/0150862 A1 | 6/2013 | Aram | |
| 2013/0184713 A1 | 7/2013 | Bjoraski | |
| 2013/0204382 A1 | 8/2013 | Walker | |
| 2013/0226190 A1 | 8/2013 | Mckinnon | |
| 2013/0261759 A1 | 10/2013 | Claypool | |
| 2013/0296874 A1 | 11/2013 | Chao | |
| 2013/0297031 A1 | 11/2013 | Hafex | |
| 2013/0297265 A1 | 11/2013 | Baloch | |
| 2014/0013565 A1 | 1/2014 | Macdonald | |
| 2014/0052268 A1 | 2/2014 | Sanford | |
| 2014/0066720 A1 | 3/2014 | Wilkinson | |
| 2014/0078139 A1 | 3/2014 | Park | |
| 2014/0081277 A1 | 3/2014 | Park | |
| 2014/0277542 A1 | 9/2014 | Stein | |

FOREIGN PATENT DOCUMENTS

| | | |
|---|---|---|
| EP | 2665428 B1 | 11/2013 |
| JP | 03674046 B2 | 7/2005 |
| JP | 2008531163 | 8/2008 |
| JP | 2013013727 | 1/2013 |
| JP | 2014504173 | 2/2014 |
| WO | 1994005212 A1 | 3/1994 |
| WO | 2009105496 A1 | 8/2009 |
| WO | 2009134672 A1 | 11/2009 |
| WO | 2010099353 A1 | 9/2010 |
| WO | 2013131066 A1 | 9/2013 |
| WO | 2013190573 A1 | 12/2013 |
| WO | 2014008444 A1 | 1/2014 |
| WO | 2014047514 A1 | 3/2014 |

OTHER PUBLICATIONS

Attune Knee System/Intuition Instruments—Surgical Technique, 2014; 0M0000 0612-10-512 REV. 1, 84 Pages.

PCT Int'l Search Report & Written Opinion PCT/US2015/051672 Dated Dec. 14, 2015, 8 Pages.

Gromov, Kirill, et al: "What is the Optimal Alignment of the Tibial and Femoral Components in Knee Arthroplasty?", Acta Orthopaedica, vol. 85, No. 5, Sep. 1, 2014 (Sep. 1, 2014), pp. 480-487, XP055232954, GB ISSN: 1745-3674, DOI: 10.3109/17453674.2014.940573, p. 481, col. 1, Paragraph 3, p. 482, col. 1, Paragraph 3—col. 2, Paragraph 7; Figure 1.

Cherian, Jeffrey J., et al: "Mechanical, Anatomical, and Kinematic Axis in TKA: Concepts and Practical Applications", Current Reviews in Musculoskeletal Medicine, vol. 7, No. 2, Mar. 27, 2014 (Mar. 27, 2014), pp. 89-95, XP055232902, US ISSN: 1935-973X, DOI: 10.1007/S12178-014-9218-Y, p. 91, col. 1-p. 91, col. 2, Figure 1, 2.

Japanese Search Report for Corresponding Japanese Application No. 2020-022233, Dated Mar. 23, 2021, 3 PAGES.

(56) References Cited

OTHER PUBLICATIONS

Indian Search Report for Corresponding Indian Application No. 201717009513, Dated Apr. 27, 2021, 7 Pages.

* cited by examiner

SURGICAL PLANNING AND METHOD

RELATED APPLICATIONS

This application is a continuation application of U.S. patent application Ser. No. 17/155,194, which was a divisional application of U.S. patent application Ser. No. 15/504,152, now U.S. Pat. No. 10,932,855, which was a national stage entry of International Patent Application No. PCT/US2015/051672 filed on Sep. 23, 2015, which claimed priority to U.S. Provisional Pat. App. Ser. No. 62/054,604 filed on Sep. 24, 2014, entitled "SURGICAL PLANNING AND METHOD," all of which are incorporated by reference herein in their entireties.

BACKGROUND

The present invention relates to total knee replacement surgery and in particular to methods of planning total knee replacement surgery and also to a workflow for a surgical method to execute a surgical plan.

Various surgical techniques for total knee replacement are generally known and used. They typically involve replacement of a distal part of the patient's femur with a femoral prosthetic implant or component and replacement of a proximal part of the patient's tibia with a tibial prosthetic implant or component. An aspect of the surgical procedure is preparing the distal part of the femur and proximal part of the tibia to provide resect bone surfaces on which the respective implants are placed. The height and angle of the resected bone surfaces determines the position of each implant relative to its respective bone which is one factor in the post-operative behaviour of the patient's knee joint. The surgeon may also carry out some soft tissue balancing which can also impact on the behaviour of the patient's knee joint.

Hence, an important aspect of the surgical procedure is the positioning of the implants relative to their respective bones and also relative to each other. A variety of philosophies can inform the surgical technique used by a surgeon. A common philosophy is to try and place the femoral implant so that it is perpendicular to an axis passing from the centre of the femoral head of the hip joint to the centre of the knee and the tibial implant so that it is perpendicular to an axis passing from the centre of the knee to the centre of the ankle. This placement means that the load line from the patient's hip to the ankle, passes through the centre of the knee and hence helps provide an even loading on the medial and lateral sides of the implants and tibia.

However, for many patients their legs may exhibit varying degrees of varus (lower leg pointing medially—sometimes colloquially known as 'bowlegged') or valgus (lower leg pointing laterally—sometimes colloquially known as 'knock knee') alignment. For varus alignment, the load bearing line between the centre of the femoral head and the centre of the ankle passes medially of the centre of the knee and for valgus, the load bearing line passes laterally of the centre of the knee. Hence, if a patient with a varus of valgus pre-operative leg alignment has total knee replacement surgery with the femoral component place perpendicular to the hip-knee axis and the tibial component placed perpendicular to the knee-ankle axis, then this will alter their overall leg alignment (making them less varus or valgus respectively). Hence, while this can lead to good mechanical performance of prosthetic components of the artificial knee joint, it can also effect the overall performance of the patient's lower limb as their post-operative leg would be slightly straighter compared to pre-operatively.

On the other hand, if an anatomy based philosophy is adopted to the surgical procedure, so that the femoral implant and tibial implant are placed so that the post-operative alignment of the leg is similar to the pre-operative alignment of the leg, for varus or valgus patients, this results in the load line passing medially or laterally of the knee centre and therefore unbalancing the forces exerted between the tibial and femoral prosthetic components and also the forces at the interfaces between the prosthetic components and their respective bones. Hence, although such an approach preserves the leg alignment of the patient, it can reduce the mechanical performance of the prosthetic components and also lead to further knee problems.

As total knee replacement procedures involve the careful positioning of the prosthetic components, irrespective of the surgical approach being used, it is known to plan at least some aspects of the surgical procedure so that the intended positions of the prosthetic components are known beforehand. The initial plan may need to be intra-operatively or iteratively adjusted depending on how other steps of the surgical procedure are executed or depending on other factors that may only become apparent during the surgical procedure, such as a more advanced disease state than expected. However, generally some form of surgical plan is often prepared and which may include intended or planned positions for the prostheses which are consistent with the intended surgical outcome.

The planning process can take a range of forms, including inspecting, measuring or marking X-ray images of the patient's bone all the way through to complex computer assisted surgical planning methods using patient bone images and/or 3D modelling techniques. The surgical planning information can sometimes also be used with computer assisted surgery systems which include surgical workflow software often providing visual or image guidance as to the position of the patient's bones, instruments and implanted being used in the surgical procedure and also a visual indication of the planned implant positions. Hence, planning software and computer assisted surgery systems can be used to help improve the accuracy of placement of implants compared to their planned positions. However, it is the underlying surgical philosophy which drives the planning process itself.

SUMMARY

The invention can provide a planning method, and/or related surgical method using the results of the planning method, which combines the otherwise competing approaches of maintaining the patients anatomy and maintaining the mechanical performance of the patient's prosthetic knee joint so as to take advantage of the respective benefits of these otherwise competing approaches.

A first aspect of the invention provides a method of carrying out a total knee replacement surgical procedure on a knee of a leg of a patient. The method may include obtaining anatomical data for the leg of the patient. The anatomical data may allow the femoral mechanical axis, the tibial mechanical axis and the joint line of the knee to be determined. A planned proximal tibial cut angle and a planned distal femoral cut angle, may be determined. The planned proximal tibial cut angle and the planned distal femoral cut angle ensure that a long leg angle between the tibial mechanical axis and the femoral mechanical axis resulting from the planned proximal tibial cut angle and the planned distal femoral cut angle is within a first pre-selected range of values and/or the planned proximal tibial cut angle is within a second pre-selected range of values. A total knee replacement procedure may be carried out on the knee of the patient. A distal femoral cut may be made using the planned distal femoral cut angle and a proximal tibial cut may be made using the planned proximal tibial cut angle.

The first and second preselected ranges of values for the long leg angle and proximal tibial cut angle respectively allow the effect of the positions of the proximal tibial cut angel and distal femoral cut angle to be checked to ensure an acceptable long leg angle and proximal tibial cut angle and adjusted, if necessary. Hence, the benefits of an anatomical approach and maintaining the patient's original anatomy can be realised together.

Determining the planned proximal tibial cut angle and the planned distal femoral cut angle may include determining if the long leg angle corresponds to an angle falling within the first pre-selected range of values.

Determining the planned proximal tibial cut angle and the planned distal femoral cut angle may further include setting an initially planned proximal tibial cut angle to restore the joint line and an initially planned distal femoral cut angle to restore the joint line.

Determining the planned proximal tibial cut angle and the planned distal femoral cut angle may further includes determining whether the initially planned proximal tibial cut angle corresponds to an angle falling within the second pre-selected range of values.

Determining the planned proximal tibial cut angle and the planned distal femoral cut angle may further include setting the planned distal femoral cut angle to the initially planned distal femoral cut angle and the planned proximal tibial cut angle to the initially planned proximal tibial cut angle when it is determined that the initially planned proximal tibial cut angle does correspond to an angle falling within the second pre-selected range of values.

Determining the planned proximal tibial cut angle and the planned distal femoral cut angle may further include setting the planned proximal tibial cut angle to the initially planned proximal tibial cut angle modified by an adjustment angle causing the planned proximal tibial cut angle to correspond to an angle falling within the second pre-selected range of values when it is determined that the initially planned proximal tibial cut angle does not corresponds to an angle falling within the second pre-selected range of values.

Determining the planned proximal tibial cut angle and the planned distal femoral cut angle may further include setting the planned distal femoral cut angle to the initially planned distal femoral cut angle modified by the adjustment angle when it is determined that the initially planned proximal tibial cut angle does not correspond to an angle falling within the second pre-selected range of values.

Determining the planned proximal tibial cut angle and the planned distal femoral cut angle may further include setting an initially planned proximal tibial cut angle to adjust the long leg angle to correspond to an angle falling within the first pre-selected range of values and/or an initially planned distal femoral cut angle to restore the joint line.

Determining the planned proximal tibial cut angle and the planned distal femoral cut angle may further include determining whether the initially planned proximal tibial cut angle corresponds to an angle falling within the second pre-selected range of values.

Determining the planned proximal tibial cut angle and the planned distal femoral cut angle may further include setting the planned distal femoral cut angle to the initially planned distal femoral cut angle and the planned proximal tibial cut angle to the initially planned proximal tibial cut angle when it is determined that the initially planned proximal tibial cut angle does correspond to an angle falling within the second pre-selected range of values.

Determining the planned proximal tibial cut angle and the planned distal femoral cut angle may further include setting the planned proximal tibial cut angle to the initially planned proximal tibial cut angle modified by an adjustment angle causing the planned proximal tibial cut angle to correspond to an angle falling within the second pre-selected range of values when it is determined that the initially planned proximal tibial cut angle does not correspond to an angle falling within the second pre-selected range of values.

Determining the planned proximal tibial cut angle and the planned distal femoral cut angle may further include setting the planned distal femoral cut angle to the initially planned distal femoral cut angle modified by the adjustment angle when it is determined that the initially planned proximal tibial cut angle does not correspond to an angle falling within the second pre-selected range of values.

Determining the planned proximal tibial cut angle and the planned distal femoral cut angle may include determining if the angle of the joint line with respect to the tibial mechanical axis corresponds to an angle falling within the second pre-selected range of values.

Determining the planned proximal tibial cut angle and the planned distal femoral cut angle may further include setting the planned proximal tibial cut angle to restore the joint line and/or an initially planned distal femoral cut angle to restore the joint line.

Determining the planned proximal tibial cut angle and the planned distal femoral cut angle may further include determining whether the long leg angle resulting from the planned proximal tibial cut angle and initially planned distal femoral cut angle corresponds to an angle falling within the first pre-selected range of values.

Determining the planned proximal tibial cut angle and the planned distal femoral cut angle may further include setting the planned distal femoral cut angle to the initially planned distal femoral cut angle when it is determined that the long leg angle resulting from the planned proximal tibial cut angle and initially planned distal femoral cut angle corresponds to an angle falling within the first pre-selected range of values.

Determining the planned proximal tibial cut angle and the planned distal femoral cut angle may further include setting the planned distal femoral cut angle to the initially planned distal femoral cut angle modified by an adjustment angle causing the resulting long leg angle to correspond to an angle falling within the first pre-selected range of values when it is determined that the long leg angle resulting from the planned proximal tibial cut angle and initially planned distal femoral cut angle does not correspond to an angle falling within the first pre-selected range of values.

Determining the planned proximal tibial cut angle and the planned distal femoral cut angle may further include setting the planned proximal tibial cut angle using an adjustment angle correspond to an angle falling within the second pre-selected range of values and setting an initially planned distal femoral cut angle using the adjustment angle.

Determining the planned proximal tibial cut angle and the planned distal femoral cut angle may further includes determining whether the long leg angle resulting from the planned proximal tibial cut angle and initially planned distal femoral cut angle corresponds to an angle falling within the first pre-selected range of values.

Determining the planned proximal tibial cut angle and the planned distal femoral cut angle may further include setting the planned distal femoral cut angle to the initially planned distal femoral cut angle when it is determined that the long leg angle resulting from the planned proximal tibial cut angle and initially planned distal femoral cut angle corresponds to an angle falling within the first pre-selected range of values.

Determining the planned proximal tibial cut angle and the planned distal femoral cut angle may further include setting the planned distal femoral cut angle to the initially planned distal femoral cut angle modified by a further adjustment angle causing the resulting long leg angle to correspond to an angle falling within the first pre-selected range of values when it is determined that the long leg angle resulting from the planned proximal tibial cut angle and initially planned distal femoral cut angle does not correspond to an angle falling within the first pre-selected range of values.

The first pre-selected range may be not more than 10°, not more than 6°, or not more than 3°.

The first pre-selected range may extend from 175° to 185°, or from 177° to 183°, or from 177° to 180°.

The first pre-selected range may extend from 170° to 180°, or from 175° to 180°, or from 177° to 180°. Hence, the first pre-selected range may correspond to neutral and varus long leg alignment angles only and not include valgus long leg alignment angles.

The second pre-selected range may be not more than 6° or not more than 3°.

The second pre-selected range may extend from 87° to 93°.

The second pre-selected range may extend from 90° to 84°, or from 90° to 87°. Hence, the second pre-selected range may correspond to neutral and varus proximal tibial cut angles and not include valgus proximal tibial cut angles.

The adjustment angle may causes the proximal tibial cut angle to correspond to the closest value of the second pre-selected range.

The adjustment angle may cause the long leg angle to correspond to the closest value of the first pre-selected range.

The further adjustment angle may cause the long leg angle to correspond to the closest value of the first pre-selected range.

The method may further comprise capturing one or more images of the patient's leg. Obtaining anatomical data may include acquiring anatomical data from the one or more images, or from image data derived from the one or more images, or from image data defining the one or more images.

The one or more images may be x-ray images.

The one or more images may be of the patient's leg in a stressed state or a loaded state or a standing state.

Obtaining anatomical data for the leg of the patient may include measuring the position of anatomical landmarks on the patient's leg.

The position of the anatomical landmarks may be measured using a computer assisted surgery system.

The determining of the planned cut angles may be carried out by a data processing device.

The total knee replacement procedure may be carried out using a computer assisted surgery system.

Carrying out the total knee replacement procedure on the knee of the patient may include setting the angle of a cutting block for a distal femoral cut to correspond to the planned distal femoral cut angle and/or setting the angle of a cutting block for a proximal tibial cut to correspond to the planned proximal tibial cut.

Setting the angle of the cutting block for a distal femoral cut may include operating an angular adjustment mechanism of the cutting block.

Setting the angle of a cutting block for a proximal tibial cut may include operating an angular adjustment mechanism of the cutting block.

A second aspect of the invention provides a method of determining a planned proximal tibial cut angle and a planned distal femoral cut angle to be used in a total knee replacement surgical procedure to be carried out on a knee of a leg of a patient. The method may comprise setting a first pre-selected range of values for a long leg angle between the tibial mechanical axis and the femoral mechanical axis. The method may also comprise setting a second pre-selected range of values for proximal tibial cut angle. A planned proximal tibial cut angle and a planned distal femoral cut angle may be determined using anatomical data obtained from the patient which defines the patient's tibial mechanical axis, femoral mechanical axis and knee joint line. The planned proximal tibial cut angle and the planned distal femoral cut angle ensures that the long leg angle resulting from the planned proximal tibial cut angle and the planned distal femoral cut angle is within the first pre-selected range of values and the planned proximal tibial cut angle is within the second pre-selected range of values.

The preferred features of the determining part of the first aspect of the invention may also be preferred features of the second aspect of the invention.

The method may be a computer implemented method.

A third aspect of the invention provides a computer readable medium storing computer program code in a non-transitory form, wherein the computer readable code is executable by a data processor to carry out the method of the second aspect of the invention and any preferred features thereof.

A fourth aspect of the invention provides a data processing device comprising a data processor; and the computer readable medium of the third aspect of the invention, and wherein the computer program code is executable by the data processor.

A fifth aspect of the invention provides a computer assisted surgery system including a data processing device according to the fourth aspect of the invention.

A sixth aspect of the invention provides a medium bearing user readable instructions enabling the user to carry out the method of the second aspect of the invention. The medium may also bear user readable instructions for carrying out any of the preferred features of the second aspect of the invention. The medium may bear an indication of the first pre-selected range of values and the second pre-selected range of values. The medium may include one or more first fields where a user can record data. The data may be anatomical data derived from the patient. The anatomical data may include the angle of the femoral mechanical axis, the angle of the tibial mechanical axis, the angle between the femoral mechanical axis and the tibial mechanical axis, the angle of the joint line, the angle between the joint line and the femoral mechanical axis and/or the angle between the joint line and the tibial mechanical axis. The medium may include one or more second fields where a user can record the result of a calculation. The result of the calculation may be a value of an angle.

BRIEF DESCRIPTION OF THE DRAWINGS

One or more embodiments of the invention will now be described in detail, by way of example only and with reference to the accompanying drawings, in which.

DETAILED DESCRIPTION OF THE INVENTION

Figure 1:
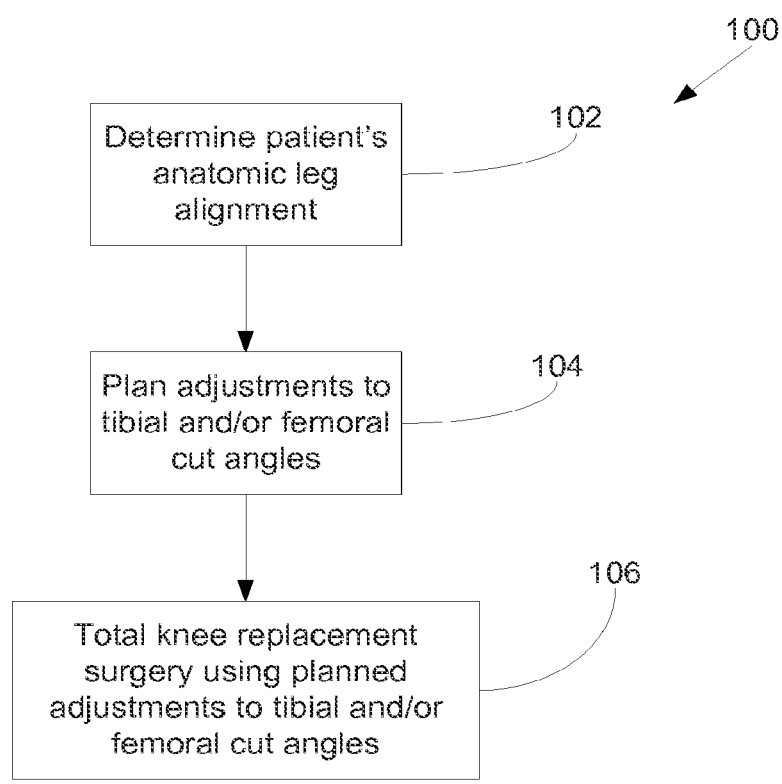
FIG. 1 is a flow chart illustrating various stages of an overall surgery related method according to an aspect of the invention.

The following detailed description sets forth numerous specific details to provide a thorough understanding of the invention. However, those skilled in the art will appreciate that the invention may be practiced without these specific details. In other instances, well known methods, procedures, components, instruments or implants have not been described in detail so as not to obscure the invention.

In the Figures like reference numerals are used for like elements unless indicated otherwise or the context requires otherwise.

With reference to FIG. 1, there is shown a high level flowchart illustrating various stages of an overall method 100 of preparing for, planning and conducting total knee replacement surgery 100. Aspects of the invention may reside in the overall method 100, the individual stages thereof, combinations of the individual stages and combinations of sub-stages of the stages illustrated in FIG. 1.

An initial stage 102 of the overall method involves determining the patient's pre-operative anatomical legal alignment 102. This may be carried out in a number of ways, as described in greater detail below, and essentially involves determining the hip, knee, ankle axes of the patient's leg and also the knee joint line. Anatomical information derived from the patient's actual leg are obtained at this initial step 102.

After the patients anatomic leg alignment information has been obtained, at step 104 a planning method according to one aspect of the invention is carried out. The planning method carried out at step 104 uses the patient's anatomic leg alignment information obtained in step 102 to determine any angular adjustments to be made to femoral and/or tibial cuts. The result of planning step 104 are planned tibial and/or femoral cut angles which can then be used in the actual surgical procedure carried out at step 106.

Hence, at step 106, a total knee replacement surgical procedure is carried out using the tibial and femoral cut positions determined from planning surgery 104 which may include adjustments to the tibial and/or femoral cut angles compared to those used in conventional procedures. The tibial and/or femoral cut angles planned at stage 104 implement a surgical philosophy underlying the surgical method step 106 that the femur is the key kinematic driver of the knee. Therefore, an improved functional restoration of the patient's knee can be achieved by resurfacing the femur within the constraints of maintaining the long leg alignment and tibial cuts angles within safe boundaries.

The pre-operative surgical planning method carried out at step 104 allows a pre-operative surgical plan to be developed that can restore the natural joint line within predefined safe boundaries of the varus or valgus angle of the tibial cut, restores the long leg alignment of the patient within predefined safe boundaries for the hip-knee-ankle axis and may also restore the natural posterior femoral condyles within predefined boundaries of femoral rotation.

The planning method of step 104 recognises that the long leg alignment of the patient is dependent on the distal femoral cut angle and tibial cut angle. The method enables calculation of a one of these variables based on second safe target ranges for the other two. The angle of the distal femoral cut and/or tibial cut can be modified to ensure that they stay within predefined ranges of values. Any adjustment to the tibial cut angle can be applied also to the femoral rotation of the knee in flexion.

The planned femoral and tibial cut angles, either of both of which may include adjustments arising from planning method 104, are then used as input to the surgical procedure 106. Surgical procedure 106 is then largely conventional and may use largely conventional instrumentation in order to carry out the total knee replacement surgery. However, the angles at which the tibial and/or femoral cutting blocks are set relative to the femur and/or tibia differ to those that would otherwise be used.

The surgical method 106 can also use any prosthetic knee implant system comprising femoral and tibial components intended for use in anatomy based surgical procedure.

For example, a suitable set of instruments include the Intuition instruments described in the Attune surgical knee system surgical technique document available from DePuySynthes, a Johnson & Johnson company (Intuition is a Trade Mark of DePuySynthes). The knee implants used may be the Attune knee system implants also available from DePuySynthes and also described in the Attune knee system surgical technique document available from DePuySynthes (Attune is a Trade Mark of DePuySynthes which may be registered in some countries). However, the invention is not limited to either very specific implants or the specific instruments of the Attune knee system. Rather, any instrumentation allowing the angle of the distal femoral cut to be adjusted relative to the femur and the tibial cut to be adjusted relative to the tibia can be used.

An exemplary surgical procedure corresponding to step 106 is described in greater detail below.

Figure 2:
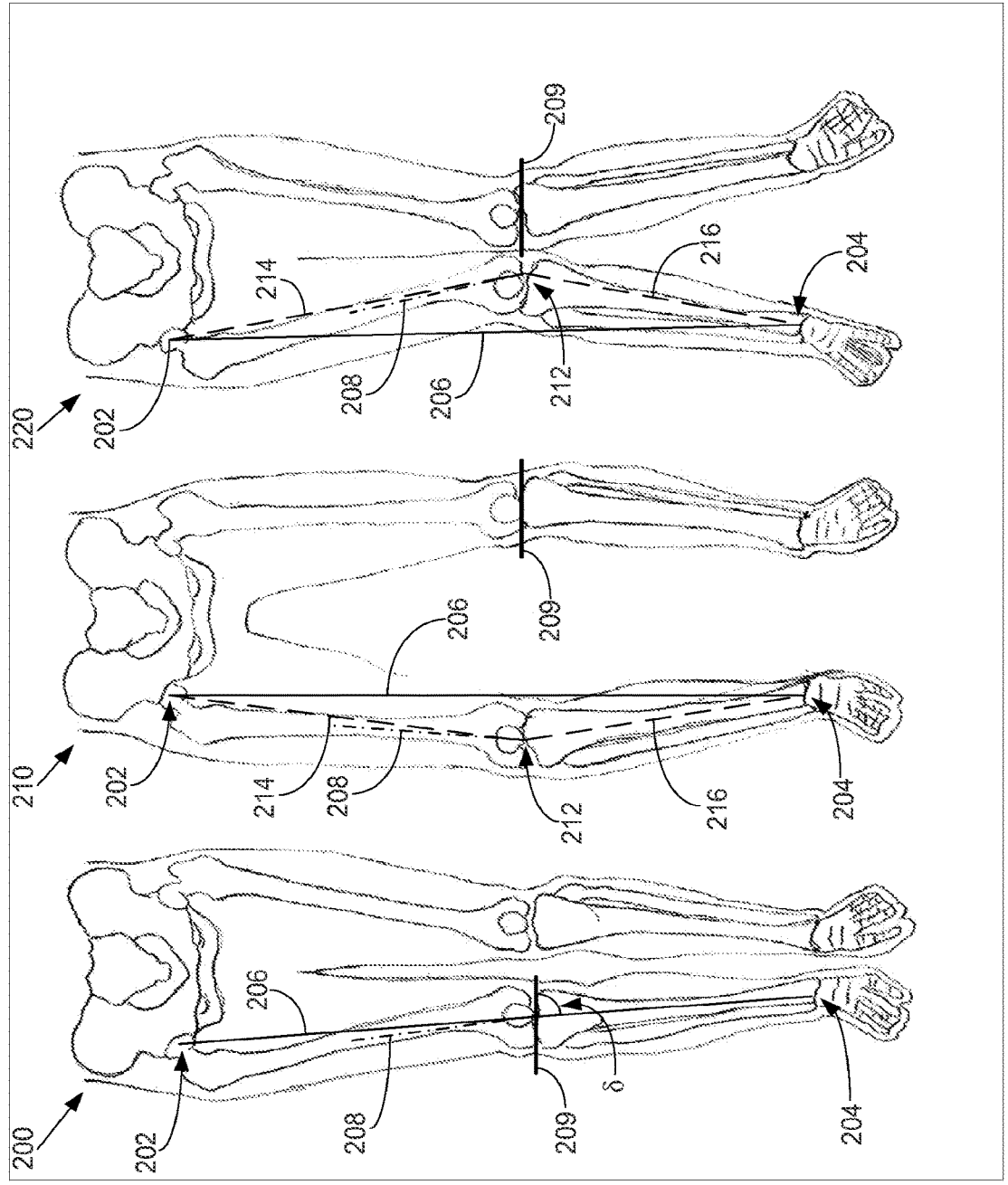
FIGS. 2A, 2B and 2C respectively show illustrations of neutral, varus and valgus leg alignments.

With reference to FIGS. 2A, 2B and 2C there are illustrated the different leg alignments possible for a human.

FIG. 2A shows a neutral leg alignment 200. A neutral leg alignment is characterised by the load bearing axis extending from the centre of the femoral head 202 to the centre of the ankle 204, represented by solid line 206, passing through the centre of the patient's knee. Also illustrated in FIG. 2A, as a dash dot line 208, is the approximate axis of the intramedullary canal of the distal end of the femur, and which represents the distal femoral anatomical axis. FIG. 2A shows the patient's leg alignment in a standing, loaded condition in which the weight of the patient's body passing along the long leg axis 206. Also shown in FIG. 2A is the joint line 209 of the patient's knee. The joint line 209 is generally parallel to the floor on which the patient is standing and typically approximately 3° offset from perpendicular to the long leg axis 206. In other words, the angle subtended between the joint line 209 and the long leg axis 206 on the medial side, and inferior to the joint line, and marked δ in FIG. 2A is typically approximately 87°.

FIG. 2A shows the various axes of the patient's leg projected on to the frontal plane of the body.

FIG. 2B is similar to FIG. 2A but shows a leg having a varus alignment. The long leg axis 206 extends from the centre of the femoral head 202 to the centre of the ankle 204. A hip-knee axis 214, also known as the femoral mechanical axis is defined by the line passing from the centre of the femoral head 202 to the centre of the knee 212. The knee-ankle axis 216, also known as the tibial mechanical axis is defined by the line running from the centre of the knee 212 to the centre of the ankle 204. As the leg has a varus alignment, the hip-knee-ankle axis defined by lines 214 and 216 is no longer co-linear with the long leg axis 206 as is the case in the neutral alignment illustrated in FIG. 2A. As can be seen in FIG. 2B, the angle on the medial side subtended between the hip-knee axis 214 and knee-ankle axis 216 is less than 180°. Conversely, the angle on the lateral side between the hip-knee axis 214 and knee-ankle axis 216 is greater than 180°. Again, line 208 represents the alignment of the intramedullary canal at the distal end of the femur.

More specifically, the hip-knee axis, or mechanical axis of the femur, 214 can be considered to extend from the centre of the femoral head to the mid-condylar point between the cruciate ligaments of the knee. The knee-ankle axis, or the mechanical axis of the tibia, 216 can be defined by the line from the centre of the tibial plateau to the centre of the tibial plafond.

FIG. 2C shows a valgus leg alignment 220. Again, the femoral mechanical axis 214 and tibial mechanical axis 216 are no longer co-linear with the long leg axis 206. However, the long leg axis 206 falls laterally of the knee for a valgus alignment whereas the long leg axis 206 falls medially of the knee for a varus alignment as shown in FIG. 2B. The angle subtended by the femoral mechanical axis 214 and tibial mechanical axis 216 medially of the knee is greater than 180° and the angle subtended by the femoral mechanical axis 214 and tibial mechanical axis 216 on the lateral side is less than 180°.

The joint line of the knee, 209, can generally be considered to be the line tangential to the distal most parts of the medial and lateral condyles. Generally, as illustrated in FIGS. 2B and 2C, the joint line 209 is substantially parallel to the floor however, the angle of the joint line relative to the mechanical axes of the tibia and femur of the knee varies in the varus and valgus alignments as will be appreciated by a person of ordinary skill in the art.

Returning to FIG. 1, at a first anatomical information gathering stage 102, information is obtained from the patient's body, either directly or indirectly, sufficient to establish the femoral mechanical axis 214, the tibial mechanical axis 216 and the joint line 209.

Indirect approaches typically involve capturing an image of the patient's bones and determining the positions of various anatomical landmarks in the bone images in order to determine the required anatomical alignment information.

For example, a long leg x-ray may be taken of the patient in a standing, loaded position. The x-ray may involve the capture of one or a plurality of x-rays which overlap, sufficient to allow the various anatomical landmark positions to be determined. From the x-ray images, the centre of the femoral head 202 can be determined as well as the centre of the knee, the centre of the ankle and also the joint line 209 corresponding to the line tangential to the distal most parts of the medial and lateral condyles.

This may simply involve marking the x-rays, drawing lines, measuring distances and either calculating or measuring angles.

In other more complex approaches, image processing routines may be used on digitised images of the x-rays or digital x-rays themselves in order to manually, automatically or semi automatically determine the required angle information.

In other embodiments, three dimensional modelling and/or computer simulation software may be used and CT scan data may be processed to determine the required anatomical information.

In a direct approach, the positions of various anatomical landmarks on the patient are determined directly on the patient themselves. This may be done by palpating the patient and measuring various distances. Also, computer assisted surgery techniques may be used in which trackable markers are attached to the patient's bones and/or instruments so as to capture the position of various anatomical landmarks by placing a trackable pointer on those landmarks. In this approach, the determination of the patient's anatomical information may be carried out as part of a surgical procedure itself, rather than a purely pre-operative step, as access to the interior of the patient's knee may be required.

Computer assisted surgery methods for determining the centre of rotation of the femoral head are generally known in the art. Examples of these include attaching a trackable marker to the patient's knee, rotating the femur about the hip joint and capturing the locus traced by the trackable marker. From this, the centre of rotation of the hip, corresponding to the centre of the femoral head can be determined.

In instances where the patient has a disease condition, such that, for example, the medial or lateral condyle has worn, then an x-ray may be captured with the lower leg in a stressed position so that the patient's knee adopts an alignment similar to that it would have in the absence of the disease condition and which can be considered more accurately to correspond to the original anatomy of the patient's knee rather than the disease state.

Other ways of obtaining information or data defining the anatomical arrangement and geometry of the patient's knee may be used and will be apparent to a person of ordinary skill in the art and from the discussion herein.

Figure 3:
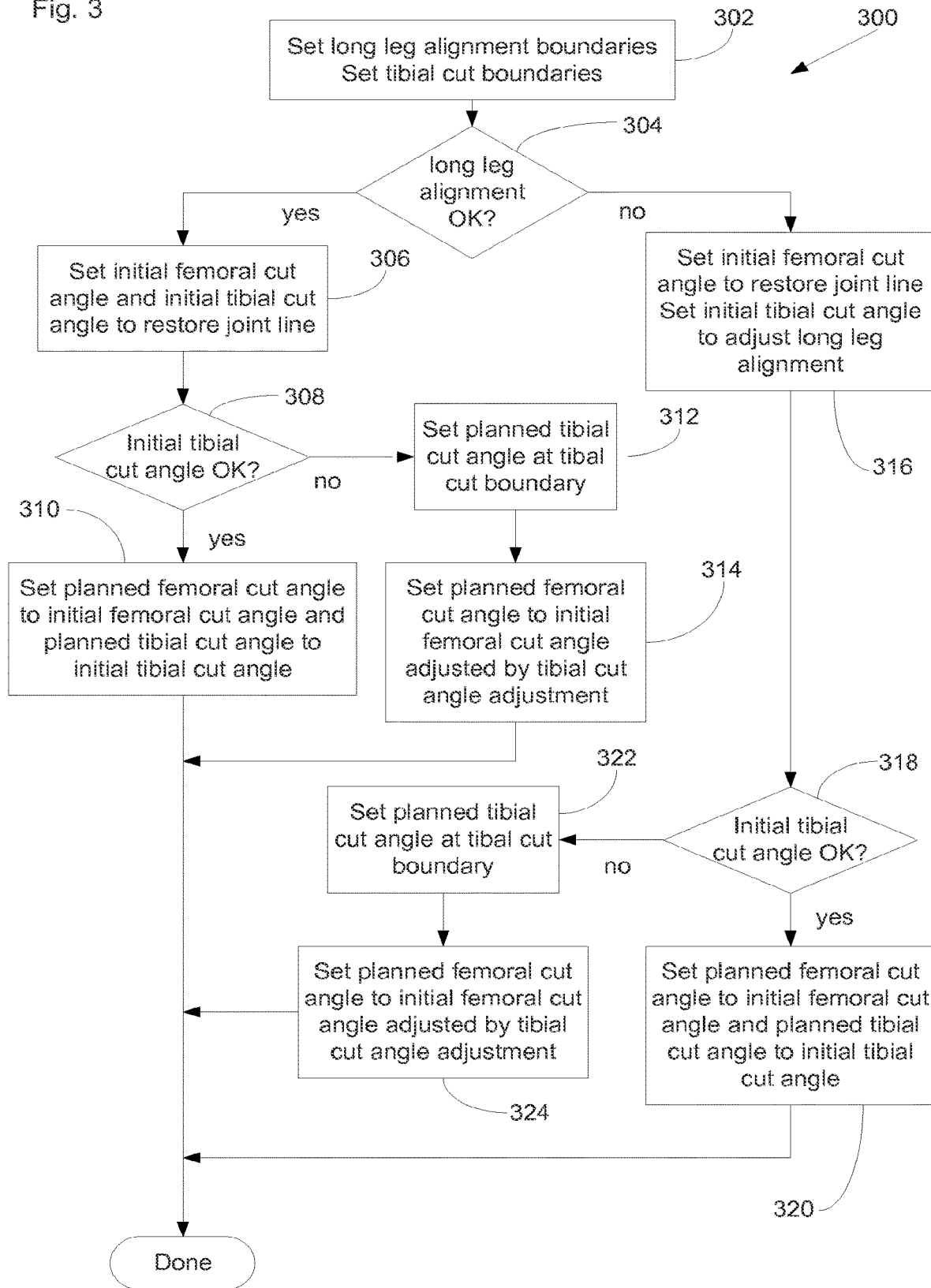
FIG. 3 shows a flow chart illustrating a first embodiment of a planning method according to an aspect of the invention.

FIG. 3 shows a process flow chart illustrating a total knee replacement planning method 300 according to an aspect of the invention and corresponding generally to step 104 of FIG. 1. Planning method 300 corresponds to a femur based planning approach which aims to maintain the angle of the femoral cut as parallel to the joint line, if possible, by modifying the tibial cut angle, if necessary, to ensure that the tibial cut angle and leg alignment are both within safe boundaries. If this cannot be done by modifying the tibial cut angle alone, then the femoral cut angle can also be modified to ensure compliance with the tibial cut angle and long leg angle safe boundaries. A tibia based planning approach is also possible and is described later with reference to FIG. 8.

Method 300 may be implemented in a number of different ways. For example, with reference to FIG. 9, method 300 may be implemented in software as part of a more general surgical planning computer program 940 which may be associated with a computer assisted surgery (CAS) system 950 or may be a standalone computer program dedicated to this purpose only, for example as an application on a smart phone or tablet or other general purpose computing device. In other embodiments, method 300 may be implemented as a set or rules, or guidelines or a flow chart on printed media to which a surgeon may refer to in order to carry out the method and enter various measurements, values and calculations used in the method. Irrespective of how the method 300 is implemented in practice its output or results are a planned tibial cut angle, a planned femoral distal cut angle and optionally a planned femoral posterior cut angle. The planning method 300 does not also plan the height of the cuts as this is not important in realising the benefits of the method, the heights or depths of the cuts may depend on the size of the implants used, the soft tissues of the knee and other factors and the heights or depths of the cuts may be determined as for a conventional total knee replacement surgical procedure.

An initial step 302 of the planning method 300 involves setting boundaries for the long leg alignment angle and the angle of the proximal tibial cut. As illustrated in FIG. 2A, for a neutral alignment, in which the femoral mechanical axis 214 and the tibial mechanical axis 216 are collinear and aligned with the long leg axis 206, the angle between the femoral mechanical axis and tibial mechanical axis is substantially 180°. Hence, at step 302 a range of acceptable leg alignment values is defined. For example, the range of acceptable angles may be 3°, and the boundary values may be 177° and 180°. For the purposes of the examples described below, the magnitude of the angle subtended by the femoral mechanical axis and the tibial mechanical axis on the medial side of the knee will be used and will be referred to herein as $\alpha$. Hence, $\alpha$ being greater than 180° corresponds to valgus alignment and $\alpha$ being less than 180° corresponds to varus alignment. However, the choice of the definition of the angle used to define the long leg alignment is largely arbitrary.

It is believed that a variation of up to 10° away from neutral alignment will still provide reasonable mechanical performance of the tibial and femoral components of the prosthetic knee. However, in other embodiments, a variation of up to not more than 3° may be used as the boundaries or limits of the long leg alignment of the patient's leg. In this example, at step 302 the long leg alignment boundaries are set such that $177° \leq \alpha \leq 180°$, and hence corresponding to neutral to varus alignments.

Figure 4:
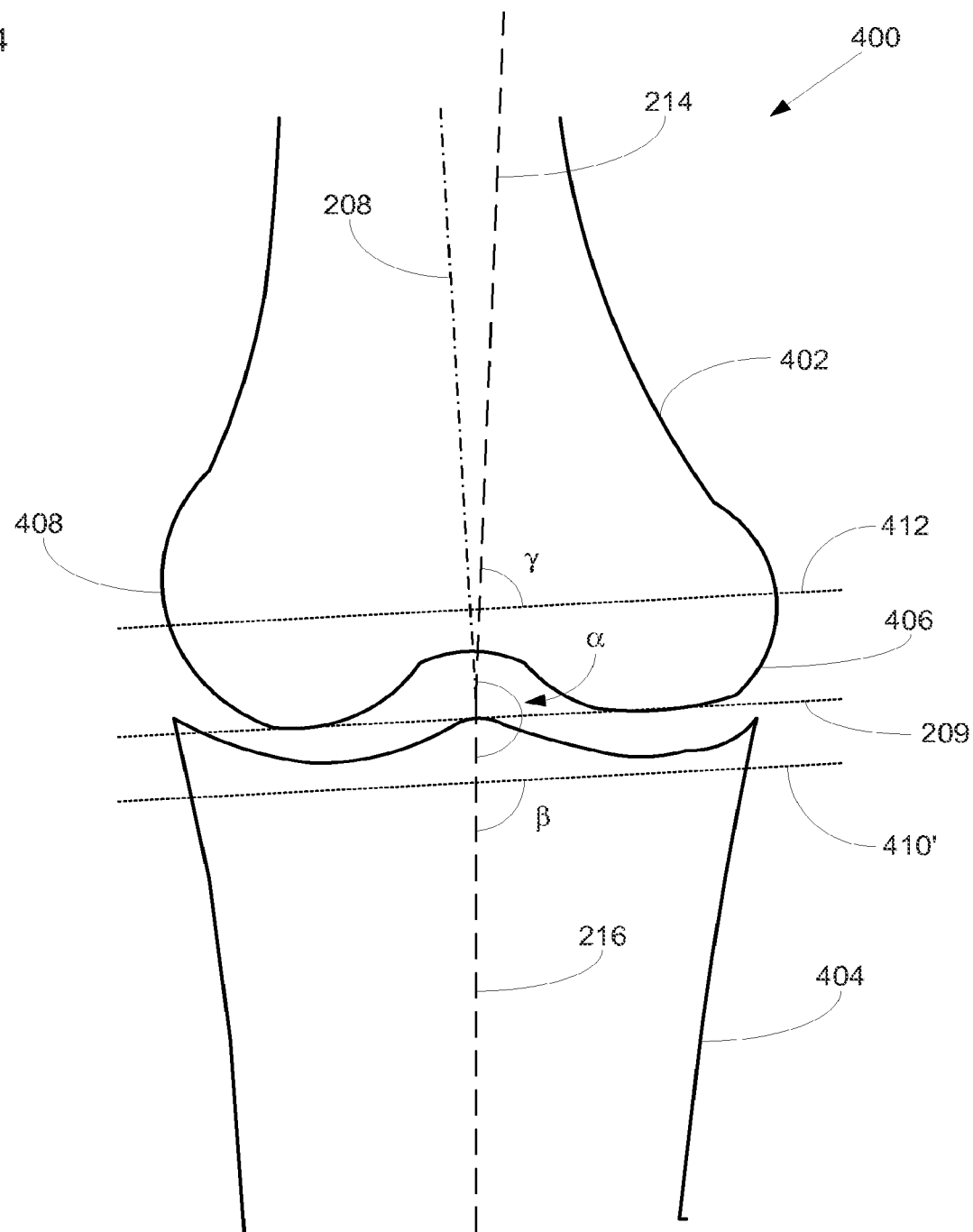
FIG. 4 is a schematic diagram of a first example knee joint geometry illustrating the method of FIG. 3.

At step 302, the boundaries for an acceptable range of values of the tibial cut angle is also set. FIG. 4 shows a schematic diagram of a patient's pre-operative knee joint 400 and includes the distal part of the femur 402 and the proximal part of the tibia 404. Also shown is the femoral anatomical axis 208 adjacent the distal part of the femur and corresponding generally to the femoral intramedullary canal. The anatomical axis of the tibia is largely coincidental to the mechanical axis of the tibia 216. Using the convention set up above for this example, the medial condyle is 406, the lateral condyle is 408 and the angle $\alpha$ is subtended by the femoral mechanical axis 214 and the tibial mechanical axis 216. The joint line 209 is tangential to the distal most parts of the medial 406 and lateral 408 condyles. The joint line angle can generally be defined as the angle, on the medial side, subtended between the joint line 209 and tibial mechanical axis 216 and inferior to the joint line. As shown in FIG. 4, the tibial cut angle can be defined as the angle subtended between the tibial cut line 410 and the tibial mechanical axis 216 inferior to the joint line and is labelled $\beta$ in FIG. 4. The definition of the tibial cut angle is again largely arbitrary and other definitions are possible, such as the angle subtended between the tibial cut line and tibial mechanical axis superior to tibial cut line 410.

A distal femoral cut angle, $\gamma$, can also be defined as the angle subtended between the distal femoral cut line 412 and the femoral mechanical axis 214. Again the definition of the distal femoral cut angle $\gamma$ is largely arbitrary, and other definitions are possible.

As discussed above, for a neutral leg alignment as illustrated in FIG. 2A, the joint line 209 is generally parallel to the floor and approximately 3° offset from perpendicular to the tibial mechanical axis (which is coincident with the long leg axis 206 for neutral alignment). The purely anatomical surgical philosophy is to simply make the tibial cut line 410 parallel to the patient's joint line 209, thereby replicating the knee geometry of neutral alignment. However, the planning method 300 instead sets a range of acceptable values for the angle of the tibial cut. In this example, the range of values is not more than 3° less than perpendicular to the tibial mechanical axis, i.e. $87° \leq \beta \leq 90°$, and hence corresponding to neutral to varus alignments. It is purely coincidence that the magnitude of the ranges of values for leg alignment angle and tibial cut angle are both 3°. In other embodiments, the magnitudes of the ranges of values may be different for leg alignment angle and tibial cut angle.

The range of acceptable angles for the long leg alignment and the proximal tibial cut angle set at step 302 may be based on a number of approaches either individually or in combination. Theoretical and/or empirical approaches may be used. For example, a more empirical approach would be to analyse survivorship data for implants in different patients and correlate that with the post-operative long leg alignment angles and/or tibial cut angles arising for the patients' implants. A more theoretical approach would be to use computer analysis of computer models of the patient's leg and knee implant to determine the distribution, direction and size of various forces. Another more empirical approach would be to measure the forces arising in a prosthetic knee for different long leg alignment angles to determine the effect of long leg alignment angle and/or proximal tibial angle on the forces in the prosthetic knee joint and/or exerted by the prosthetic knee joint on the patient's resected tibia and/or femur. The results of theoretical and empirical approaches may be combined to help determine the preselected ranges of angles used at step 302.

As noted above, the definitions of the various angles are arbitrary to an extent. The boundaries of the ranges of values of the long leg angle and tibial cut angle are set at step 302. When these ranges are used to determine whether the long leg angle and tibial cut angel requirements are met, this may be a direct comparison, if the ranges and angles are defined in the same way or it may be an indirect comparison, if the ranges and angels are defined in different way. This direct or indirect comparison is covered by determining whether the various angles correspond to an angle falling within or outside the ranges. Hence, this encompasses situations in which the definitions are the same or differ, in which case a transformation may need to be applied to make the angles directly comparable with the ranges, for example adding or subtracting 180° or 90°.

In the following example, the definitions of the angles and values used in the ranges are the same and therefore allow a direct comparison when determining whether various angles correspond to an angle within the first or second ranges of values set at 302. Returning to FIG. 3, at step 304, the patients anatomical data obtained previously at step 102, is used to determine whether the patient's long leg alignment is with the boundaries set at step 302. The angle between the patient's femoral mechanical axis 214 and their tibial mechanical axis, $\alpha$, is compared with the range of acceptable values set at step 302. In a first example, $\alpha$=178, i.e. slightly varus, and so is greater than 177° and so the long leg alignment is determined to be acceptable at step 304. The method proceeds to step 306 at which initial planned femoral cut and tibial cut angles are set. The initially planned tibial cut angle is set to an angle that would restore the joint line 209 of the patient. Hence, the initially planned tibial cut angle, between the tibial cut line 410 and the tibial mechanical axis 216, is set to make the tibial cut line 410 parallel to the joint line 209, which in this example is 89°. Similarly, the initially planned femoral cut angle $\gamma$ is set to a value such that the distal femoral cut line 412 is parallel to the joint line and in this case also to the initially planned tibial cut line 410'. Hence, in this example the initially planned femoral cut angle is 89°.

At step 308 it is determined if the initially planned value for the tibial cut angle is within the boundaries set at step 302. Hence, step 308 determines whether, the initially planned tibial cut angle value of 89° is between 87° and 90° which it is. Hence, at step 310 the final planned femoral cut angle value is set to the initially planned value of 89° and the final planned tibial cut value is set to the initially planned value of 89° and planning is complete. Hence, the initially planned tibial and distal femoral cut angles have been validated by the planning method as being acceptable final planned cut angles.

Figure 5:
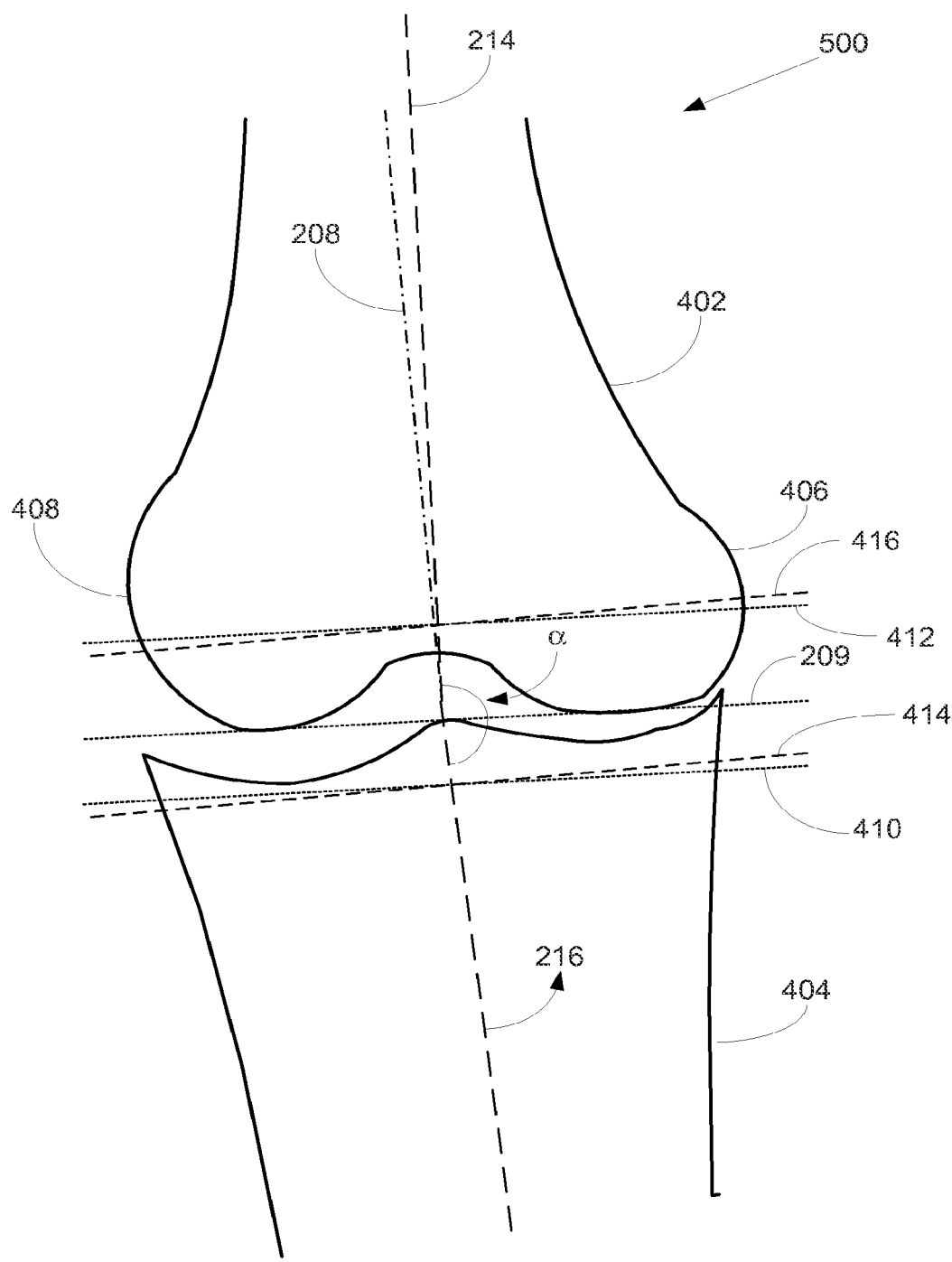
FIG. 5 is a schematic diagram of a second example knee joint geometry illustrating the method of FIG. 3.

A second example illustrates the planning method 300 further. FIG. 5 shows a different patient's knee geometry 500. In this knee geometry the value of the angle $\alpha$ between the femoral mechanical axis 214 and the tibial mechanical axis 216 is again 178° and so the method proceeds at step 304 to step 306. In this knee geometry, the angle between the joint line 209 and the tibial mechanical axis 216 is 86°. Hence, at step 306, the initially planned tibial cut angle value to restore the patient's joint line 209 will be 86° (so that the tibial cut line 410 is parallel to the joint line 209). Also, the initially planned femoral cut angle value is set so that the femoral cut line 412 is also parallel to the joint line 209. In this example, the initially planned femoral cut angle value is 92°. At step 308 it is determined if the initially planned tibial cut angle is within the boundaries set in step 302 and in this example it is not as 86° is less than the lower limit of 87°. Hence, the method proceeds to step 312. At step 312, the initially planned tibial cut angle value is set to the boundary value closest to the initially planned value, i.e. to 87° at step 314. Hence, an adjustment angle of 1° is applied to the initially planned tibial cut angle to arrive at the final planned tibial cut angle. This is illustrated in FIG. 5, by the corresponding final planned tibial cut line 414 which is no longer parallel to joint line 209 (and which is exaggerated in FIG. 5 for clarity of explanation).

As the planed angle of tibial cut has been changed, the initially planned femoral cut line 412 will no longer be parallel to the finally planned tibial cut line 414 and hence, the alignment of the leg would be altered. Hence, at step 314, the finally planned femoral cut angle is set to the initially planned femoral cut angle but adjusted by the tibial cut adjustment angle of 1°. Hence, in this example, the value of the finally planned femoral cut angle is set to 91° and gives rise to a corresponding finally planned femoral cut line 416 which is no longer parallel to joint line 209, but is parallel to finally planned tibial cut line 414 and hence does not change the leg alignment of the patient. So in this example, the finally planned tibial cut angle and distal femoral cut angles no longer provide exact replication of the pre-operative patient anatomy, as the resulting joint line will be 1° rotated compared to original anatomic joint line 209, but they are as close as possible within the boundaries set. However, the long leg alignment has not been altered and therefore this aspect of the patient's anatomy will be preserved by these planned cut angles. Hence, in this example, the initially planned femoral cut angle is modified only if the initially planned tibial cut angle is outside of the acceptable range.

Figure 6:
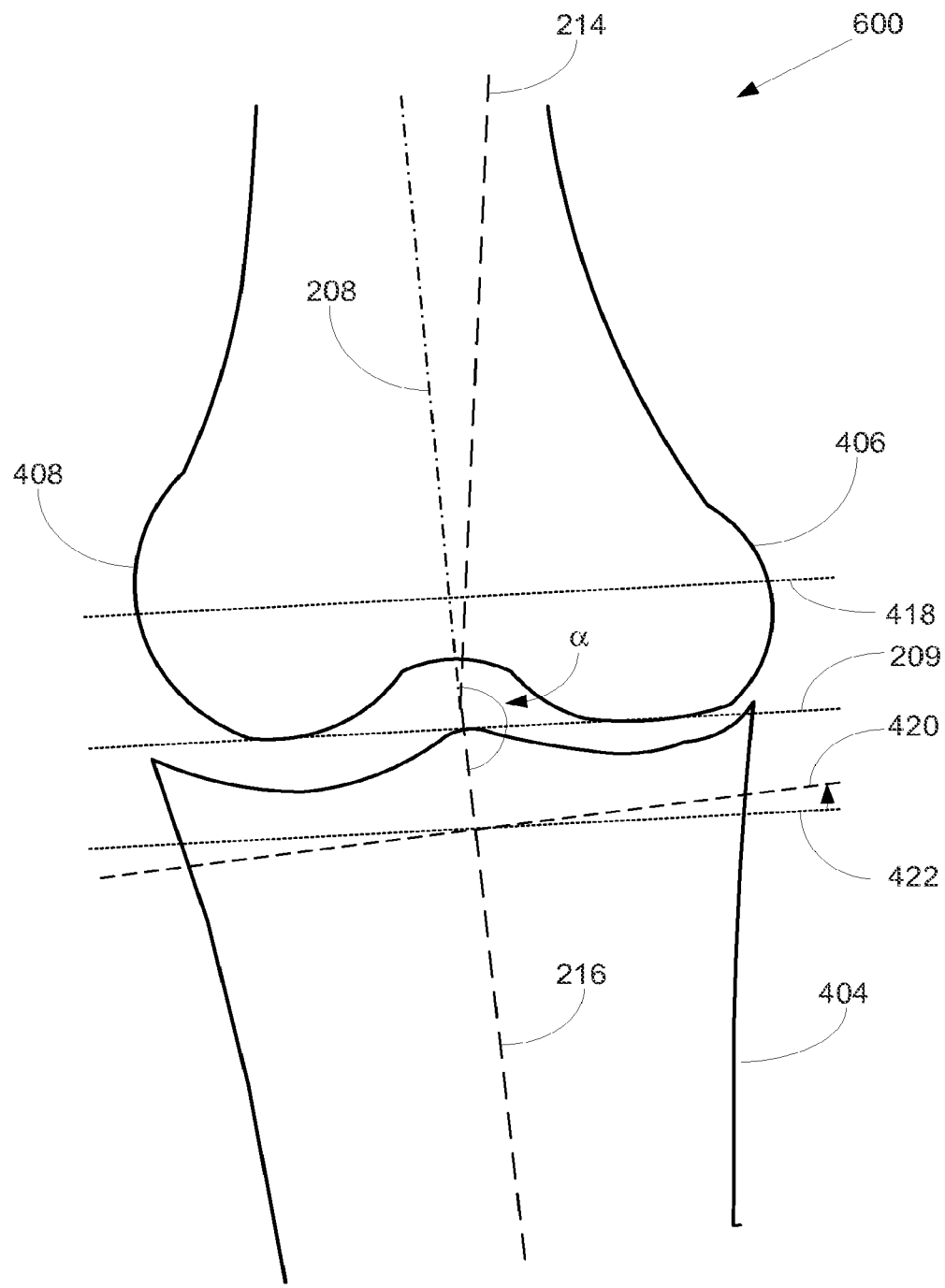
FIG. 6 is a schematic diagram of a third example knee joint geometry illustrating the method of FIG. 3.

A third example illustrates the planning method 300 further. FIG. 6 shows a different patient's knee geometry 600. In this knee geometry the value of the angle $\alpha$ between the femoral mechanical axis 214 and the tibial mechanical axis 216 is 176°. Hence, at step 304 it is determined that the long leg alignment is not within the long leg alignment boundary set at step 302, as 176°<177°. Hence, the method 300 proceeds to step 316. At step 316, the initially planned femoral cut angle is set to restore the joint line 209. In this example, the initially planned femoral cut angle is set to a value of 87° so that the corresponding initially planned femoral cut line 418 is parallel to joint line 209. Also at step 316, an initially planned tibial cut angle is set which will bring the long leg alignment back within the boundary set in step 302. Hence, as the lower limit of the long leg alignment range is 177°, a 1° rotation is added to the initially planned tibial cut angle, which is illustrated in FIG. 6, by the initially planned tibial cut line 420 being rotated by 1° relative to a line 422 parallel to the joint line 209. The initially planned tibial cut angle value, including the 1° adjustment, is therefore 90°. At step 318 it is determined whether the initially planned tibial cut angle is within the tibial cut angle boundaries set in step 302, which in this example it is. Hence, the method proceeds to step 320 at which the value of the finally planned femoral cut angle is set to the initially planned value of 87° and the value of the finally planned tibial cut angle is set to the initially planned value, which includes the 1° adjustment, of 91°. Hence, as the finally planned cut lines 418, 420 are no longer parallel (in this example by 1°) the leg alignment angle $\alpha$ has been increased by 1° and hence the long leg alignment has been brought back within the acceptable range.

Figure 7:
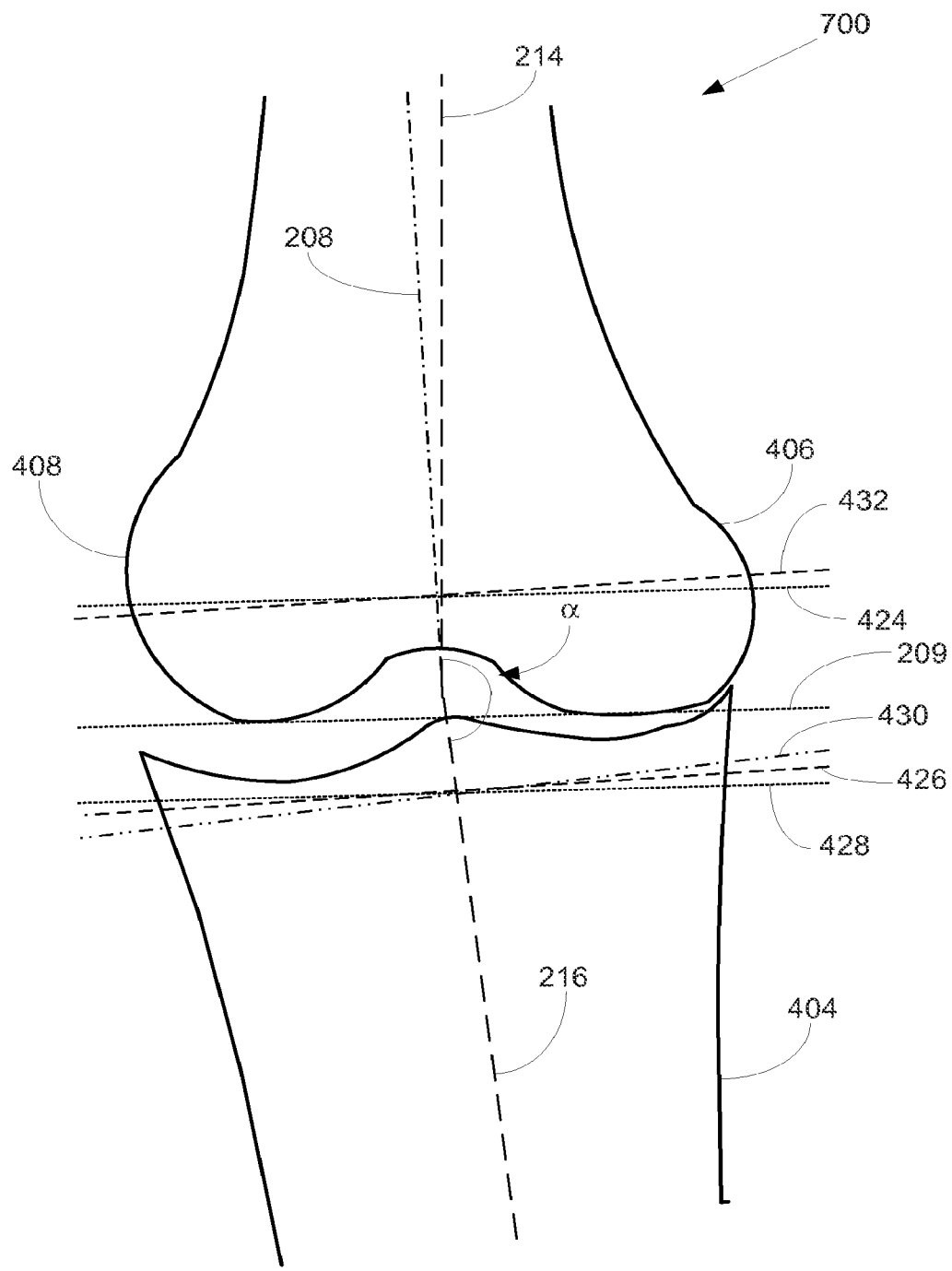
FIG. 7 is a schematic diagram of a fourth example knee joint geometry illustrating the method of FIG. 3.

A fourth example illustrates the planning method 300 further. FIG. 7 shows a different patient's knee geometry 700. In this knee geometry the value of the angle $\alpha$ between the femoral mechanical axis 214 and the tibial mechanical axis 216 is 176°. Hence, at step 304 it is determined that the long leg alignment is not within the long leg alignment boundary set at step 302, as 176°<177°. Hence, the method 300 proceeds to step 316. At step 316, the initially planned femoral cut angle is set to restore the joint line 209. In this example, the initially planned femoral cut angle is set to a value of 91° so that the corresponding initially planned femoral cut line 424 is parallel to joint line 209. Also at step 316, an initially planned tibial cut angle is set which will bring the long leg alignment back within the boundary set in step 302. Hence, as the lower limit of the long leg alignment range is 177°, a 1° rotation is added to the initially planned tibial cut angle, which is illustrated in FIG. 7, by the initially planned tibial cut line 426 being rotated by 1° relative to a line 428 parallel to the joint line 209. The initially planned tibial cut angle value, including the 1° adjustment, is therefore 86°. At step 318 it is determined whether the initially planned tibial cut angle is within the tibial cut angle boundaries set in step 302, which in this example it is not as 86°<87°. Hence, the method proceeds to step 322 at which the value of the finally planned tibial cut angle is set to the closest tibial cut boundary, being 87°, and therefore including an adjustment angle of 1°. This is illustrated in FIG. 7, by corresponding finally planned tibial cut line 430, being rotated by a further 1° from the initially planned tibial cut line 426. The method proceeds to step 324 at which the value of the finally planned femoral cut angle is set to the initially planned femoral cut angel but adjusted by the tibial cut angle adjustment of 1° needed to bring the tibial cut angle back within the acceptable range. Hence, the finally planned femoral cut angle is set to the value of 92°. This is illustrated in FIG. 7, by corresponding finally planned femoral cut line 432, being rotated by a further adjustment angle of 1° from the initially planned femoral cut line 424. Hence, as the finally planned cut lines 430, 432 are no longer parallel (in this example by 1°) the leg alignment angle α has been increased by 1° and hence the long leg alignment has been brought back within the acceptable range and also the tibial cut angle has been brought back to within the acceptable range. However, the femoral cut angle has been adjusted away from that which would recreate the joint line.

It will be appreciated that FIGS. 4 to 7 are intended merely to help illustrate the specific angles and geometries described in the text, and the Figures do not themselves necessarily have the same actual angles of the examples described above.

The embodiment of the planning method illustrated in FIG. 3 prioritises the angle of the distal femoral cut as the method tries to maintain the femoral cut line parallel to the joint line, and preferentially modifies the angle of the tibial cut. For example, the tibial cut angle, rather than the femoral cut angle, is used to modify the long leg alignment axis if that is outside its boundaries. The femoral cut angle is only modified in cases where the tibial cut angle would otherwise be outside its boundaries, in which case the femoral cut angel is adjusted by the same amount of angle as the tibial cut angle is adjusted to bring it back within its boundaries.

Alternatively, the invention may also be implemented as a tibial cut prioritised plan using a similar approach but in which the proximal tibial cut angle is preserved as an anatomical cut (i.e. to recreate the joint line) unless needed in order to keep the tibial cut angle within the acceptable boundaries. The tibial based planning method 800 is illustrated by the flow chart shown in FIG. 8. The planning method 800 illustrated in FIG. 8 uses the same overall approach as the planning method 300 illustrated in FIG. 3 of setting leg alignment and tibial cut boundaries and then checking that the tibial cut angle and leg length alignment fall within those boundaries, and if not then adjusting the tibial cut and/or femoral cut angles so that the finally planned tibial and femoral cut angles result in a knee joint geometry that does fall within those boundaries. However, the approach of the method 800 differs in that it initially sets the tibial cut angle as the finally planned tibial cut angle and then only the femoral cut angle is subsequently adjusted, if necessary to bring the leg length alignment within its acceptable boundaries.

At step 802, the boundaries of the leg length alignment are set, e.g. $177° \leq \alpha \leq 180°$, and the boundaries of the tibial cut angle relative to the tibial mechanical axis are set, e.g. $87° \leq \beta \leq 90°$. At step 804, the angle between the joint line and the tibial mechanical axis is compared to the tibial cut angle boundaries, to see if an anatomical approach, i.e. the tibial cut replicating the patient's joint line, is acceptable. If so, then at step 806, the planned tibial cut angle is set to the angle resulting in the tibial cut line being parallel to the joint line and also the initially planned femoral cut angle is set so that the distal femoral cut line will also be parallel to the joint line. At 808, it is determined if the angle between the femoral mechanical axis and the tibial mechanical axis is within the boundaries set at 802. If the long leg alignment is determined to be within the boundaries at 808, then the finally planned femoral cut angle is set to the initially planned femoral cut angle at 810 and the planning is complete. The result is hence a planned distal femoral cut and a planned tibial cut each being parallel to the patient's joint line and hence reproducing the patient's original anatomy, while also ensuring appropriate mechanical operation of the prosthetic knee joint.

Returning to step 808, if the long leg alignment is determined not to be within the boundaries at 808, then the finally planned femoral cut angle is set to the initially planned femoral cut angle but adjusted to bring the long leg alignment back within the boundaries at 812. For example, if the angle between the patient's femoral mechanical axis and tibial mechanical axis is 175°, then a 2° adjustment at least is needed to bring the long leg alignment back within the boundaries. Hence, at step 812, a 2° adjustment is made to the initially planned femoral cut angle and that value is then used as the finally planned femoral cut angle. Hence, planning is complete and results in an anatomy preserving tibial cut, but a slight change in the long leg alignment of the patient.

Returning to step 804, if it is determined that the angle between the joint line and tibial mechanical axis is outside the tibial cut boundaries, e.g. is 85°, then at step 814, the tibial cut angle is planned as being the closest boundary value, i.e. 87°. It will be appreciated that by choosing the closest boundary value, as is also done in method 300, the adjustments made away from the patient's anatomy are minimised, thereby helping to preserve the benefits arising from anatomy based surgical philosophies. Also at 814, the initially planned femoral cut angle is set to that needed to restore the joint line, but also including the tibia cut adjustment angle. Hence, the initially planned femoral cut angle is set as including the 2° tibial adjustment angle at 814. Hence, the planned tibial cut line and initially planned femoral cut line are parallel at this stage of the method. However, the long leg alignment angle has now been adjusted, by 2° in this example. At 816 it is determined if the angle between the tibial mechanical axis and the femoral mechanical axis that would arise from the planned tibial cut angle and the initially planned femoral cut angle is within the acceptable boundary. If originally, the long leg angle was 175°, then the adjusted long leg angle at this stage would be 177° and therefore within the boundaries. Hence, at 816, the method proceeds to 818 and the planned femoral cut angle is set to the initially planned femoral cut angle, which includes the 2° adjustment. Hence, the planned tibial cut line is left as close as the boundaries allow to the anatomical cut line, and a minimal adjustment to the long leg alignment so as to be within the acceptable boundaries has been introduced.

Returning to step 816, if originally, the long leg angle was 174°, then the adjusted long leg angle at this stage would be 176° and therefore outside the boundaries. Hence, at 816, the method proceeds to 820 and the planned femoral cut angle is set to the initially planned femoral cut angle but including an angular adjustment to bring the long leg alignment back within the boundaries. Hence, a further 1 adjustment is added to the initially planned femoral cut angle, to bring the corresponding long leg alignment axis to 177° and therefore within the boundary. Hence, the planned tibial cut line is left as close as the boundaries allow to the anatomical cut line, and a minimal adjustment to the long leg alignment so as to be within the acceptable boundaries has been introduced, but which is slightly greater than that of the preceding example.

Figure 8:
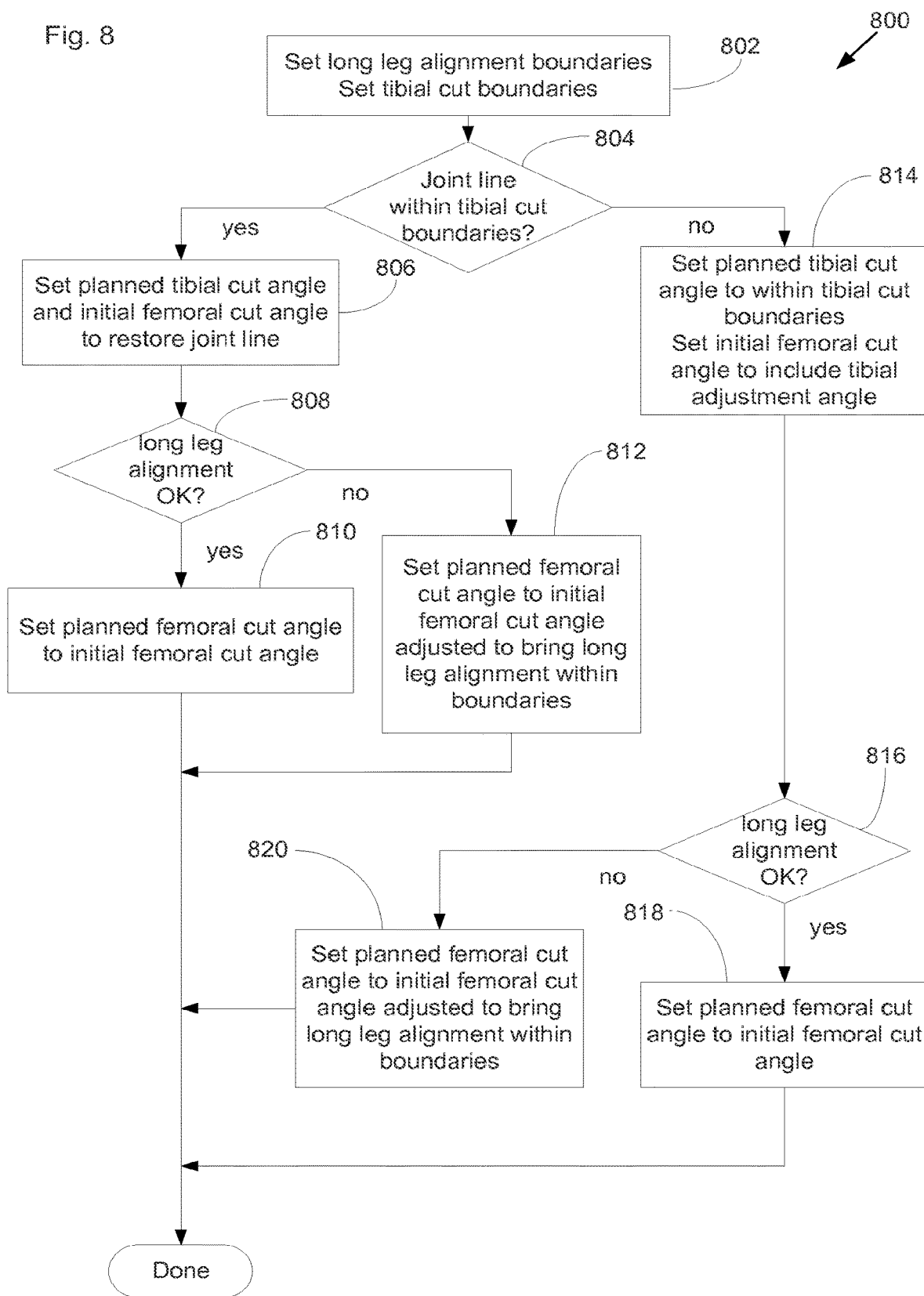
FIG. 8 shows a flow chart illustrating a second embodiment of a planning method according to an aspect of the invention.

In some embodiments, the planning methods 300 and 800 may be embodied or implemented in a printed medium which bears instructions readable by a user and guiding the user through the steps of the planning methods 300 and 800 illustrated in FIGS. 3 and 8, or other steps which ultimately implement the planning method of the invention as illustrated by the specific methods of FIGS. 3 and 8. The instructions may include written instructions as well as instructions in graphical form, such as one or more diagrams of a knee joint showing the various axes and angles used in the planning methods 300, 800.

The printed medium may also bear an indication of the first pre-selected range of values, e.g. $177° \leq \alpha \leq 180°$, and the second pre-selected range of values, $87° \leq \beta \leq 90°$. The medium may also include one or more first fields where a user can record a first type of data. The first type of data may be anatomical data derived from the patient and may include the angle of the femoral mechanical axis, the angle of the tibial mechanical axis, the angle between the femoral mechanical axis and the tibial mechanical axis, the angle of the joint line, the angle between the joint line and the femoral mechanical axis and/or the angle between the joint line and the tibial mechanical axis. The anatomical data should include at least enough data to allow the angles of the joint line relative to the tibial mechanical axis to be determined and also the angle between the tibial and femoral mechanical axes. The medium may include one or more second fields where a user can record the result of a calculation. The result of the calculation may be a value of an angle. Hence, at various places on the medium, fields may be provided near instructions to add or subtract various angles to enter the result of that calculation so as to maintain a record of the initially planned angles, any angular adjustments applied by following the planning methods and also the resulting finally planned tibial and femoral cut angles.

Referring back to FIG. 1, having described the surgical planning carried out at 104, a method of carrying out total knee replacement surgery using the planned tibial and femoral cut angles, corresponding to step 101, will now be described with reference to FIG. 9. As mentioned above the planning method 104 and surgical method 106 can be used for any total knee replacement system suitable for mechanical axis alignment. Also, the surgical method is largely conventional other than the angular adjustments to the planned tibial and femoral cut angles and hence largely conventional surgical instrumentation can be used. A number of conventional surgical steps are therefore not described in order not to obscure the invention. As an example only, the surgical method 106 may be carried out using the Attune Knee System and Intuition instruments as provided by DePuySynthes and as described in the Attune Knee System Surgical Technique document also provided by DePuySynthes (ATTUNE is a Trade Mark of DePuySynthes, which is registered in some countries and INTUITION is a Trade Mark of DePuySynthes).

Figure 9:
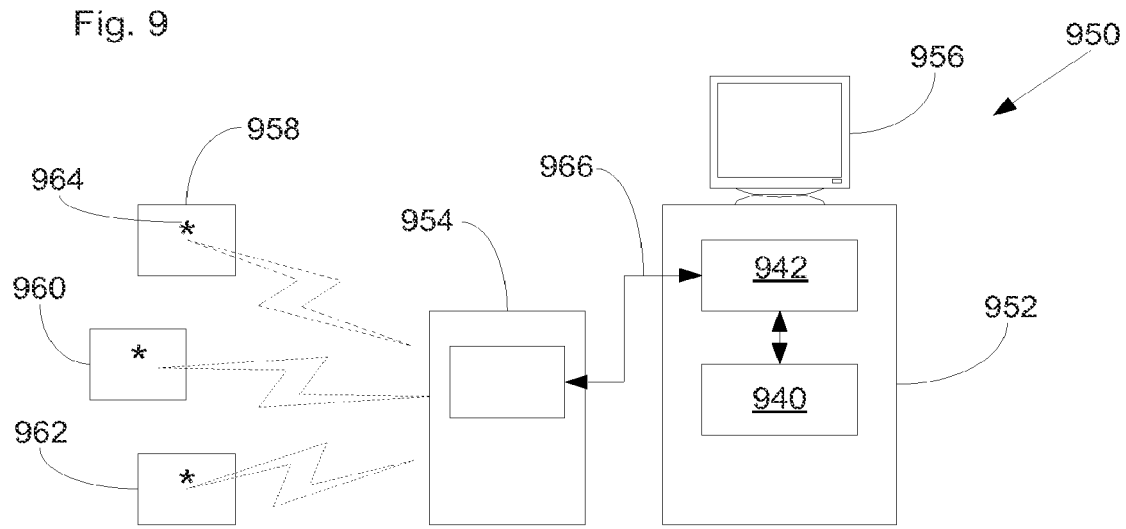
FIG. 9 shows a schematic block diagram of a computer assisted surgery system in according to an aspect of the invention and which can be used to carry out or implement the surgical method of the invention.
Figure 10:
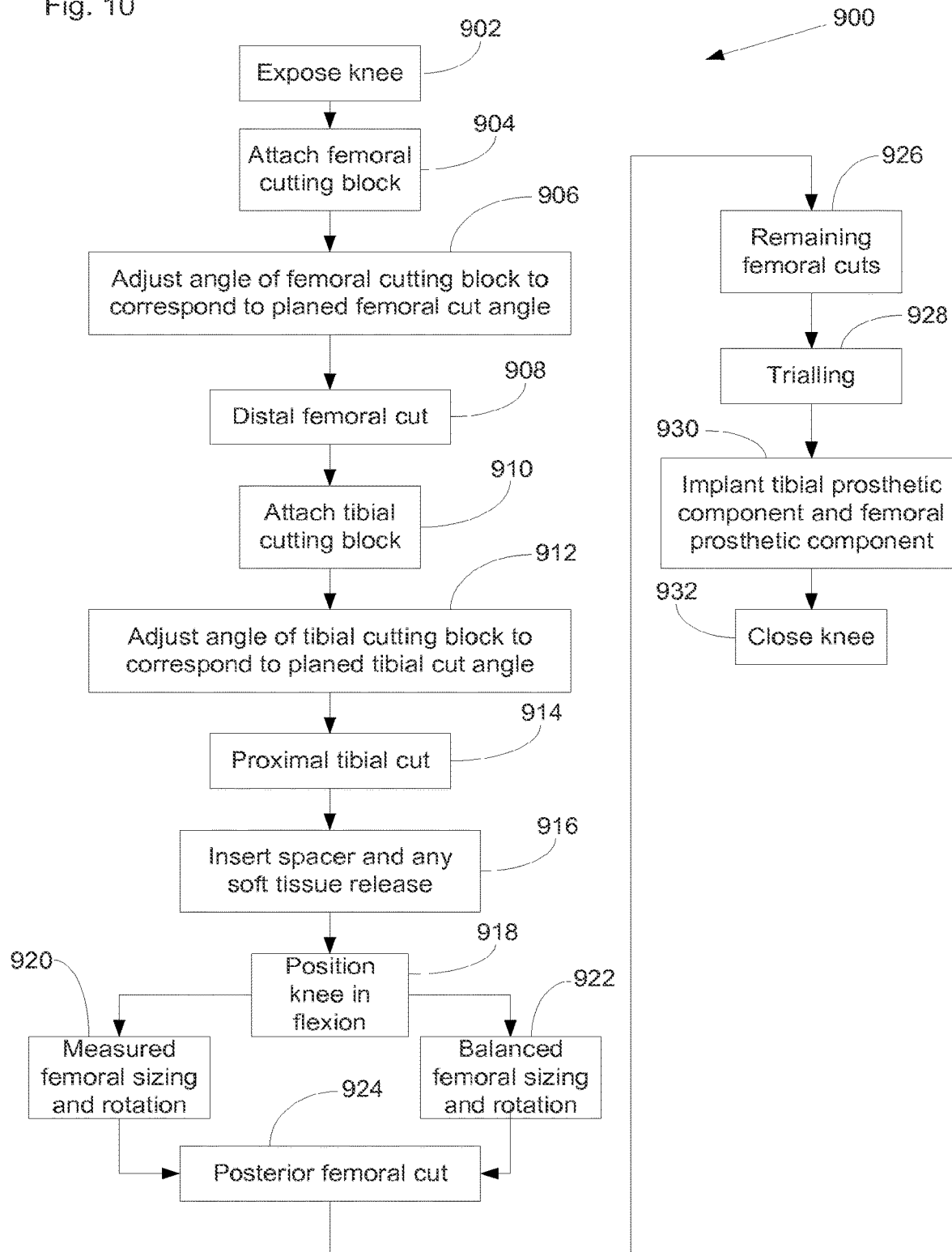
FIG. 10 shows a flow chart illustrating a surgical method part of the invention.

In some embodiments the surgical method may be carried out using a computer assisted surgery (CAS) system 950, for example as illustrated in FIG. 9. CAS systems are generally known and typically including a computer system 952, tracking system 954 and a display 956 which provides visual and other guidance to the surgeon to guide them through the various steps of the workflow of the surgical procedure and also provides guidance as to the relative positions of tools, instruments, implants and body parts, represented by 958, 960, 962, to asset in the carrying out of various acts, such as positing instrumentation, making cuts, and placing trial components and prosthetic components. The body parts and the tools, instruments and implants used in the CAS system may include one or more markers 964 which are trackable by the tracking system 954 which provides positional information or data 966 to the computer system 952. Various different types of tracking technology can be used such as wired or wireless, including infra-red, optical, acoustic or magnetic. Hence, a CAS system may including software 942 which configures the CAS system to assist the surgeon to carry out the surgical steps illustrated in FIG. 9. The CAS system may also include planning software 940 which configures the CAS system to implement the planning method used at step 104. Hence, the tibial and femoral cut planning data generated by the planning software 940 may be passed to the surgery workflow software 942 and used by the surgery workflow software 942 to provide an indication of the planned position of the tibial and femoral cuts and any angular adjustments or settings to be used with the femoral and tibial cutting block so as to reproduce the planned tibial and femoral cut positions on the display 956. Although the tracking system 954 is shown separately in FIG. 9 for the sake of explanation, it will be appreciated that the tracking system 954 can be integrated into the computer system 952 to provide a unified CAS system 950 in other embodiments.

The surgical method 900 begins at 902 by opening the patent's knee with the patient's leg generally extended. After any preparation of the surgical site, at 904 a femoral cutting block may be attached to the patient's femur. This may involve drilling a hole into the distal end of the femur to access the femoral intramedullary canal which defines the local anatomical axis of the femur. An intramedullary rod with an angle adjustable jig is connected to a distal femoral cutting block inserted into the intramedullary canal. A suitable arrangement is the distal femoral jig assembly as shown in the Attune Surgical Technique document.

As noted in FIGS. 4 to 7 above, the anatomical axis of the femur 208 is offset from the mechanical axis of the femur 214 by an angle that varies from patient to patient, depending largely on the length of their femur. For a shorter femur the angle is typically about 3°-4°, for a medium femur typically about 5°, and for a longer femur, typically about 6°-7°. As the femoral cut angle is defined in the planning stage 104 relative to the femoral mechanical axis 214, the angular offset between the anatomical axis 208 and the mechanical axis is taken into account in determining the angel to be set using the adjustable jig so as to set the correct planned position of the distal cutting block. This is because the angular position of the cutting block is typically defined relative to the anatomical axis (along which the intramedullary rod passes), such that a zero degree angle of the adjustment jig corresponds to the distal cut line being perpendicular to the femur's anatomical axis.

Hence, at step 906, the angle of the jig is adjusted so as to place the distal femoral cutting block so that the distal femoral cut line corresponds to the planned distal femoral cut angle, taking into account the offset between the mechanical axis and anatomical axis of the femur. The depth of the femoral cut will depend on the size of the implant being used and is often in the range of 4 to 16 mm, with 8-11 mm being typical. The distal femoral cutting block is then pinned in position, the femoral jig and IM rod removed and then the distal femoral cut is made at 908.

At 910, the tibial cutting block is attached to the tibia. The tibial mechanical axis and anatomical axis are usually coincidental and so usually there is no angular off set to be taken in to account for the tibial cutting block adjustment. A tibial alignment guide can be used to position and attach the tibial cutting block. A stable tibial alignment guide is described in the Attune Surgical Technique document. The tibial alignment guide is attached to the lower leg of the patient by attaching a first end to the patient's ankle and aligned with the second toe of the patient's foot and the mechanical axis of the tibia. A tibial cutting block is attached to the second end of the alignment guide and includes a central aperture through which a bone pin is placed aligned with the centre or midpoint of the knee. The medial-lateral position of the first end of the alignment guide is adjustable and when varied causes the tibial cutting block to pivot about the bone pin. Hence, at 912 the angle of the tibial cutting block can be adjusted by changing the medial-lateral position of the first end of the tibial alignment guide, until the cutting block angle corresponds to the planned tibial cut line. The tibial cutting block is then pinned in place and the proximal cut is made at 914.

It will be appreciated that in other embodiments, the order of making the distal femoral cut and the proximal tibial cut can be reversed, and steps 904 to 908 may be carried out after steps 910 to 914, with any appropriate modifications to the surgical steps resulting therefrom, and which modifications will be apparent to a person of ordinary skill in the art.

Hence, the distal femoral cut and proximal tibial cuts have now been made, but using the planned cut orientations obtained from the planning step 104 rather than conventionally planned positions. The planed tibial an femoral cut orientations help to ensure proper mechanical operation of the prosthetic knee while also maintaining the long leg alignment and anatomy of the patient as much as possible.

At 916 a spacer instrument may be inserted into the extension gap between the resected tibia and femur to assess the gap and any soft tissue release may be carried out to provide balance with the knee in extension. Soft tissue release may be more likely to be required in instances where the long leg alignment has been altered.

At 918, the knee may be articulated into flexion to allow femoral sizing and rotation to be assessed. Two different approaches may be used. A measured femoral sizing and rotation approach may be used as indicated by step 920. A measured femoral sizing and rotation guide as described in the Attune Surgical Technique document may be used. The size of the femur may be determined and the position of the femoral cutting block used to make the rest of the femoral cuts can be determined. A stylus attached to the guide can be used to determine the size of the femur. The guide is angle adjustable to allow the angular position of the femoral cutting block to be set on the resected distal femoral surface. If the angle of the tibial cut was not adjusted during planning and corresponds to the joint angle, then no change to the rotation of the femur may be introduced at this stage. The rotation of the femur is defined by the line tangential to the posterior most parts of the lateral and medial condyles. It is generally desirable for the angular relationship between this line and the plane of the resected proximal tibia to be kept the same. Hence, if an angular adjustment of the tibial cut was introduce during planning, e.g. 3°, to bring the tibial cut angle and/or the long leg alignment back within their boundaries, then the same angular adjustment is added to the femoral rotation. Hence, the femoral cutting block is rotated by an extra 3° to maintain the angular relationship between the posterior part of the condyles and the plane of the proximal tibial surface before being pinned to the resected distal femur.

Hence, a feature of the planning method may also include planning an angle of a posterior femoral cut to set the femoral rotation and which includes any angular adjustments made to the tibial cut angle during the planning method 104.

An alternative to step 920 is to use a balanced approach, rather than a measured approach, to femoral sizing and rotation at step 922. A balancing device, for example including a pair of spreaders, is used and introduced into the flexion gap to apply an equal force to the posterior parts of the medial and lateral condyles. The surgeon then positions a cutting block at an angle such that, when the posterior condyles are under load, the posterior cut is generally parallel to the plane of the resected tibial surface. Hence, in this approach, the soft tissue structure define the femoral rotation rather than the angle of the posterior femoral cut.

After the femoral cutting block has been positioned, using either the measured approach 920, which may include applying an angular adjustment to the cutting block position, or using the balanced approach of 922, at 924, the posterior femoral cut is made at 924.

After the posterior femoral cut has been made at 924, a spacer block may be inserted in the flexion gap and the balance of the joint may be assessed and any soft tissue release carried out to improve the balance of the joint.

The rest of the surgical procedure is then largely conventional. The remaining femoral cuts are made at 926 to complete preparation of the femur. Trial implants may be attached during a trialing stage 928 and a trial reduction of the joint carried out. As will be appreciated trialing can give rise to iterative changes to the cuts and/or soft tissues until the surgeon is happy. Eventually, the prosthetic tibial and femoral components are implanted at 930 and then the knee is closed 932.

As noted above the invention may include various operations from each of the general patient data acquisition 102, planning 104 and surgical method 106 steps of FIG. 1. Also, the planning method may be implemented in a variety of ways ranging from software to printed media providing instructions to guide a user through the planning method and/or including fields for entering information or data and/or carrying out calculations to determine the planned tibial and femoral cut angles.

Generally, some embodiments of some of the aspects of the invention, for example some embodiments the planning and/or surgical method, may employ various processes involving data stored in or transferred through one or more computer systems. Embodiments of the present invention also relate to an apparatus for performing these operations. This apparatus may be specially constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 11:
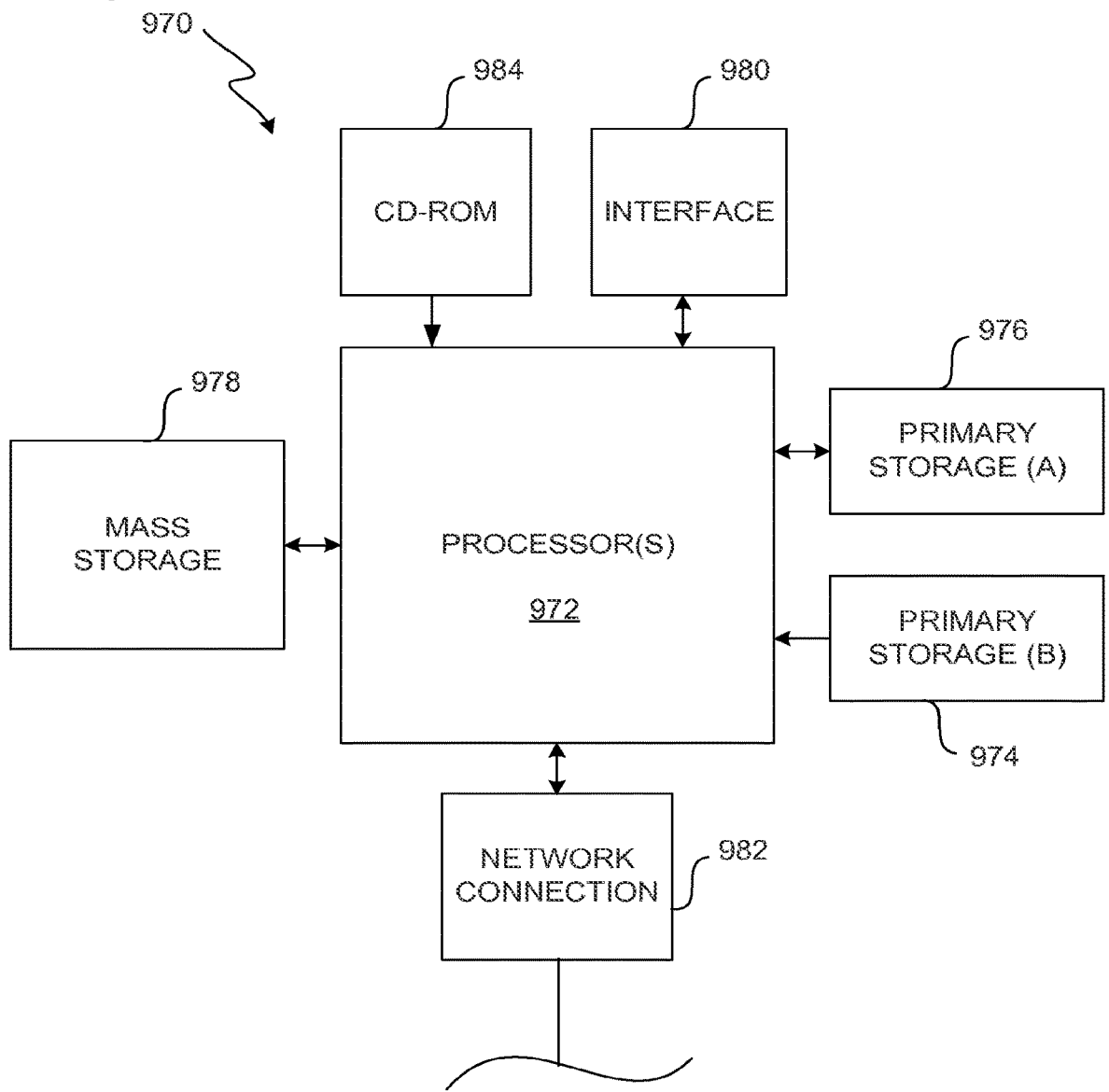
FIG. 11 shows a schematic block diagram of a data processing device according to an aspect of the invention and which can also be used in the computer assisted surgery system shown in FIG. 9.

FIG. 11 illustrates a typical computer system that, when appropriately configured or designed, can serve as a planning computer or CAS computer or part of a CAS system according to the invention. The computer system 970 includes any number of processors 972 (also referred to as central processing units, or CPUs) that are coupled to storage devices including primary storage 976 (typically a random access memory, or RAM), primary storage 974 (typically a read only memory, or ROM). CPU 972 may be of various types including microcontrollers and microprocessors such as programmable devices (e.g., CPLDs and FPGAs) and unprogrammable devices such as gate array ASICs or general purpose microprocessors. As is well known in the art, primary storage 974 acts to transfer data and instructions uni-directionally to the CPU and primary storage 976 is used typically to transfer data and instructions in a bi-directional manner. Both of these primary storage devices may include any suitable computer-readable media such as those described above. A mass storage device 978 is also coupled bi-directionally to CPU 972 and provides additional data storage capacity and may include any of the computer-readable media described above. Mass storage device 978 may be used to store programs, data and the like and is typically a secondary storage medium such as a hard disk. It will be appreciated that the information retained within the mass storage device 978, may, in appropriate cases, be incorporated in standard fashion as part of primary storage 497 as virtual memory. A specific mass storage device such as a CD-ROM 974 may also pass data uni-directionally to the CPU.

CPU 972 is also coupled to an interface 980 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 972 optionally may be coupled to an external device such as a tracking system, a database or a computer or telecommunications network using an external connection as shown generally at 982. With such a connection, it is contemplated that the CPU might receive information from the tracking system, network, or might output information to the tracking system, network or other device in the course of performing the method steps described herein.

Although the above has generally described the present invention according to specific planning methods and surgical procedures, the present invention has a much broader range of applicability. One of ordinary skill in the art would recognize other variants, modifications and alternatives in light of the foregoing discussion.

The invention claimed is:

1. A method of carrying out a surgical procedure on a knee of a leg of a patient, comprising:
   obtaining anatomical data for the leg of the patient, wherein the anatomical data allows a femoral mechanical axis, a tibial mechanical axis, and a joint line of the knee to be determined,
   setting a range for a final long leg angle between the tibial mechanical axis and the femoral mechanical axis,
   setting boundaries for a final proximal tibial cut angle,
   determining a long leg angle between the tibial mechanical axis and the femoral mechanical axis from the anatomical data,
   setting a planned distal femoral cut angle to make a final planned joint line equal to the joint line determined from the anatomical data,
   setting a planned proximal tibial cut angle to adjust the long leg angle to a final planned long leg angle within the range for the final long leg angle,
   determining whether the planned proximal tibial cut angle is within the boundaries for the final proximal tibial cut angle,
   setting the planned proximal tibial cut angle as a final planned proximal tibial cut angle when the planned proximal tibial cut angle is within the boundaries for the final proximal tibial cut angle,
   setting the planned distal femoral cut angle as the final planned distal femoral cut angle when the planned proximal tibial cut angle is within the boundaries for the final proximal tibial cut angle, and
   carrying out a surgical procedure on the knee of the patient, wherein a distal femoral cut is made along a planned femoral cut line using the final planned distal femoral cut angle and a proximal tibial cut is made along a planned tibial cut line using the final planned proximal tibial cut angle, the planned femoral cut line being not parallel with the planned tibial cut line.

2. A method of carrying out a surgical procedure on a knee of a leg of a patient, comprising:
   obtaining anatomical data for the leg of the patient, wherein the anatomical data allows a femoral mechanical axis, a tibial mechanical axis, and a joint line of the knee to be determined,
   setting a range for a final long leg angle between the tibial mechanical axis and the femoral mechanical axis,
   setting boundaries for a final proximal tibial cut angle,
   determining a long leg angle between the tibial mechanical axis and the femoral mechanical axis from the anatomical data,
   setting a planned distal femoral cut angle to make a final planned joint line equal to the joint line determined from the anatomical data,
   setting a planned proximal tibial cut angle to adjust the long leg angle to a final planned long leg angle within the range for the final long leg angle,
   determining whether the planned proximal tibial cut angle is within the boundaries for the final proximal tibial cut angle,
   determining a tibial cut angle adjustment required to change the planned proximal tibial cut angle to an angle at or within the boundaries for the final proximal tibial cut angle,
   applying the tibial cut angle adjustment to change the planned proximal tibial cut angle to a final planned proximal tibial cut angle,
   determining a final planned distal femoral cut angle based on the planned distal femoral cut angle and the final planned proximal tibial cut angle, and
   carrying out a surgical procedure on the knee of the patient, wherein a distal femoral cut is made along a planned femoral cut line using the final planned distal femoral cut angle and a proximal tibial cut is made along a planned tibial cut line using the final planned proximal tibial cut angle, the planned femoral cut line being not parallel with the planned tibial cut line.

3. The method of claim 2, wherein determining the final planned distal femoral cut angle based on the planned distal femoral cut angle and the final planned proximal tibial cut angle includes applying the tibial cut angle adjustment to change the planned distal femoral cut angle to the final planned distal femoral cut angle.

\* \* \* \* \*